US010137005B2

(12) United States Patent
Ashleigh

(10) Patent No.: US 10,137,005 B2
(45) Date of Patent: Nov. 27, 2018

(54) DEVICE AND METHOD FOR DEPLOYMENT OF AN ANCHORING DEVICE FOR INTERVERTEBRAL SPINAL FUSION

(71) Applicant: GLOBUS MEDICAL, INC., Audubon, PA (US)

(72) Inventor: Michael Ashleigh, Chester Springs, PA (US)

(73) Assignee: Globus Medical, Inc., Audubon, PA (US)

(*) Notice: Subject to any disclaimer, the term of this patent is extended or adjusted under 35 U.S.C. 154(b) by 466 days.

(21) Appl. No.: 14/881,703

(22) Filed: Oct. 13, 2015

(65) Prior Publication Data

US 2016/0338845 A1    Nov. 24, 2016

Related U.S. Application Data

(63) Continuation-in-part of application No. 14/718,514, filed on May 21, 2015.

(51) Int. Cl.
| *A61F 2/44* | (2006.01) |
| *A61F 2/46* | (2006.01) |
| *A61F 2/30* | (2006.01) |
| *A61F 2/28* | (2006.01) |

(52) U.S. Cl.
CPC ............ *A61F 2/447* (2013.01); *A61F 2/4611* (2013.01); *A61F 2/30749* (2013.01); *A61F 2002/2835* (2013.01); *A61F 2002/3035* (2013.01); *A61F 2002/30261* (2013.01); *A61F 2002/30382* (2013.01); *A61F 2002/30387* (2013.01); *A61F 2002/30398* (2013.01); *A61F 2002/30507* (2013.01); *A61F 2002/30556* (2013.01); *A61F 2002/30571* (2013.01); *A61F 2002/30579* (2013.01); *A61F 2002/30904* (2013.01); *A61F 2002/4627* (2013.01)

(58) Field of Classification Search
CPC .......... A61F 2/44; A61F 2/4455; A61F 2/447; A61F 2002/4475
See application file for complete search history.

(56) References Cited

U.S. PATENT DOCUMENTS

| 4,636,217 A | * | 1/1987 | Ogilvie | ..................... A61F 2/44 606/247 |
| 5,800,550 A | * | 9/1998 | Sertich | ..................... A61F 2/447 606/247 |
| 5,849,004 A | * | 12/1998 | Bramlet | ............. A61B 17/0401 606/232 |

(Continued)

FOREIGN PATENT DOCUMENTS

| CH | 708531 A2 | 3/2015 |
| EP | 1378202 A1 | 1/2004 |

(Continued)

*Primary Examiner* — Eric S Gibson

(57) ABSTRACT

A device and methods for intervertebral spinal fusion of adjacent intervertebral bodies. An intervertebral spacer is positioned within a narrow disc space between adjacent intervertebral bodies of a patient. The spacer is arranged with upper and lower guides. The guides are adapted to simultaneously guide the deployment of upper and lower anchors of an anchoring device into their respective intervertebral bodies. The spacer is also adapted to lock the upper and lower anchors to the spacer in the deployed position.

18 Claims, 35 Drawing Sheets

(56) References Cited

U.S. PATENT DOCUMENTS

| | | | |
|---|---|---|---|
| 6,447,546 B1 | 9/2002 | Bramlet et al. | |
| 7,695,516 B2 | 4/2010 | Zeegers | |
| 7,846,188 B2 * | 12/2010 | Moskowitz | A61B 17/0642 |
| | | | 606/279 |
| 8,257,443 B2 * | 9/2012 | Kamran | A61F 2/4465 |
| | | | 623/17.16 |
| 8,343,219 B2 | 1/2013 | Allain et al. | |
| 8,460,388 B2 | 6/2013 | Kirwan et al. | |
| 8,545,563 B2 * | 10/2013 | Brun | A61F 2/447 |
| | | | 606/99 |
| 8,617,245 B2 * | 12/2013 | Brett | A61F 2/442 |
| | | | 623/17.16 |
| 8,641,766 B2 | 2/2014 | Donner et al. | |
| 8,685,104 B2 * | 4/2014 | Lee | A61F 2/447 |
| | | | 623/17.11 |
| 8,968,405 B2 * | 3/2015 | Kirwan | A61F 2/4455 |
| | | | 623/17.11 |
| 9,039,774 B2 | 5/2015 | Chataigner et al. | |
| 9,044,337 B2 | 6/2015 | Dinville et al. | |
| 9,138,331 B2 * | 9/2015 | Aferzon | A61F 2/442 |
| 9,161,842 B2 | 10/2015 | Chin et al. | |
| 9,173,745 B2 | 11/2015 | Dinville et al. | |
| 9,517,144 B2 * | 12/2016 | McAtamney | A61F 2/4455 |
| 9,566,165 B2 * | 2/2017 | Lee | A61F 2/4425 |
| 9,707,100 B2 * | 7/2017 | Duffield | A61F 2/4611 |
| 9,757,252 B2 * | 9/2017 | Lee | A61F 2/4611 |
| 9,877,842 B2 * | 1/2018 | Chataigner | A61F 2/4455 |
| 9,925,059 B2 * | 3/2018 | Chataigner | A61F 2/4455 |
| 2003/0187436 A1 | 10/2003 | Bolger et al. | |
| 2005/0049590 A1 | 3/2005 | Alleyne et al. | |
| 2007/0270960 A1 | 11/2007 | Bonin, Jr. et al. | |
| 2009/0105832 A1 * | 4/2009 | Allain | A61B 17/0642 |
| | | | 623/17.16 |
| 2009/0138082 A1 * | 5/2009 | Reah | A61B 17/7059 |
| | | | 623/13.14 |
| 2009/0265007 A1 | 10/2009 | Colleran | |
| 2010/0160984 A1 * | 6/2010 | Berry | A61F 2/4465 |
| | | | 606/86 A |
| 2010/0161057 A1 * | 6/2010 | Berry | A61F 2/4465 |
| | | | 623/17.16 |
| 2010/0185289 A1 * | 7/2010 | Kirwan | A61F 2/4455 |
| | | | 623/17.11 |
| 2011/0178599 A1 | 7/2011 | Brett | |
| 2012/0078371 A1 | 3/2012 | Gamache et al. | |
| 2012/0116466 A1 * | 5/2012 | Dinville | A61F 2/447 |
| | | | 606/86 A |
| 2012/0150229 A1 | 6/2012 | Hess | |
| 2012/0197404 A1 * | 8/2012 | Brun | A61F 2/447 |
| | | | 623/17.16 |
| 2013/0150968 A1 * | 6/2013 | Dinville | A61F 2/447 |
| | | | 623/17.16 |
| 2013/0226300 A1 * | 8/2013 | Chataigner | A61F 2/442 |
| | | | 623/17.16 |
| 2013/0245767 A1 * | 9/2013 | Lee | A61F 2/447 |
| | | | 623/17.16 |
| 2014/0088711 A1 | 3/2014 | Chin et al. | |
| 2014/0100662 A1 * | 4/2014 | Patterson | A61F 2/4455 |
| | | | 623/17.16 |
| 2014/0180417 A1 * | 6/2014 | Bergey | A61F 2/4455 |
| | | | 623/17.16 |
| 2015/0051702 A1 * | 2/2015 | Chataigner | A61F 2/442 |
| | | | 623/17.16 |
| 2015/0057754 A1 | 2/2015 | Reed et al. | |
| 2015/0127107 A1 * | 5/2015 | Kim | A61F 2/447 |
| | | | 623/17.16 |
| 2015/0209089 A1 * | 7/2015 | Chataigner | A61F 2/4425 |
| | | | 623/17.16 |
| 2015/0305887 A1 * | 10/2015 | McAtamney | A61F 2/4455 |
| | | | 623/17.16 |
| 2015/0320568 A1 * | 11/2015 | Ameil | A61F 2/447 |
| | | | 623/17.13 |
| 2016/0338845 A1 * | 11/2016 | Ashleigh | A61F 2/447 |
| 2016/0338850 A1 * | 11/2016 | Ashleigh | A61F 2/4455 |
| 2017/0196699 A1 * | 7/2017 | Ashleigh | A61F 2/447 |

FOREIGN PATENT DOCUMENTS

| | | |
|---|---|---|
| WO | 9942062 A1 | 8/1999 |
| WO | 2012117312 A2 | 9/2012 |
| WO | 2015164707 A1 | 10/2015 |

* cited by examiner

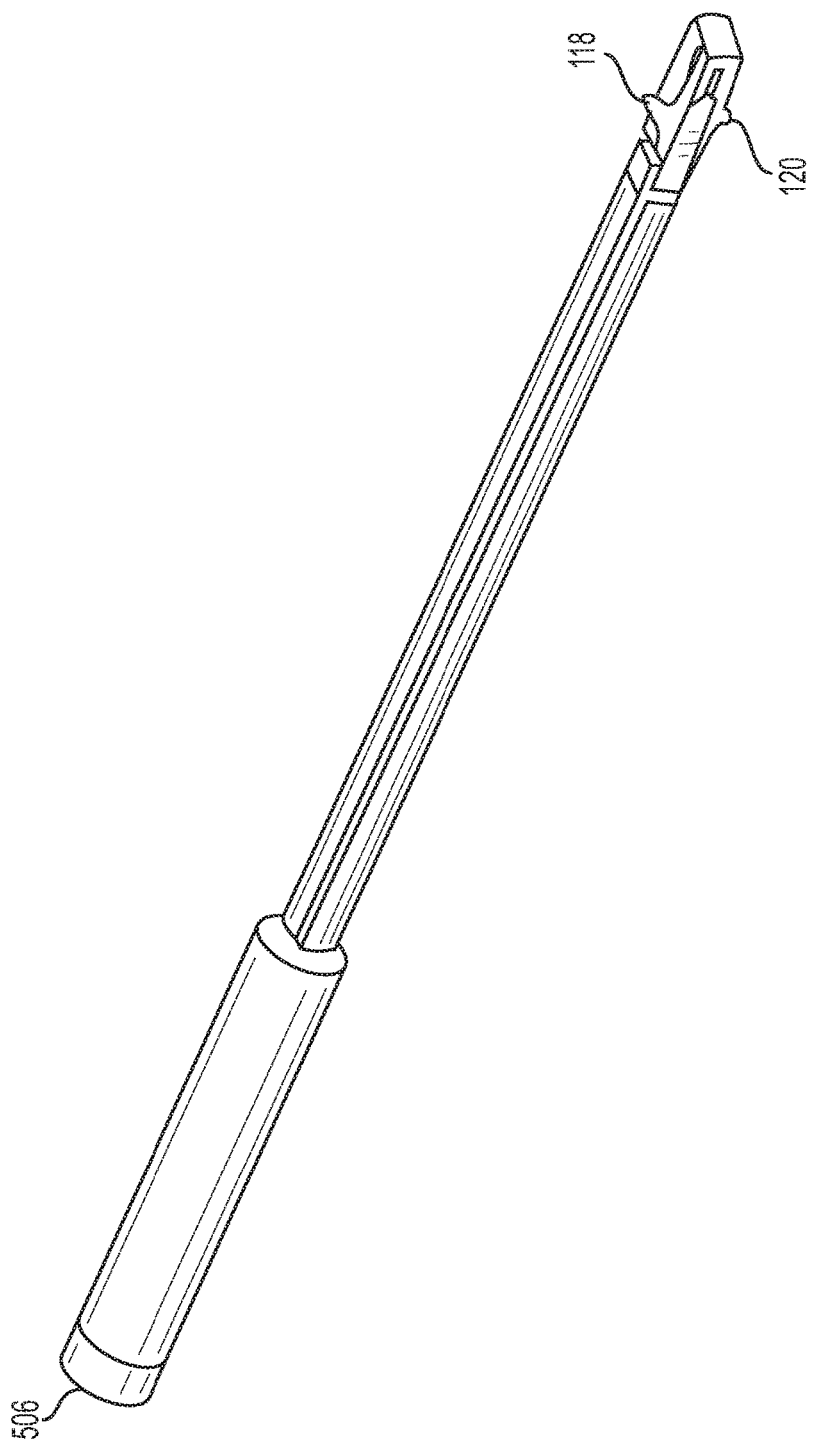

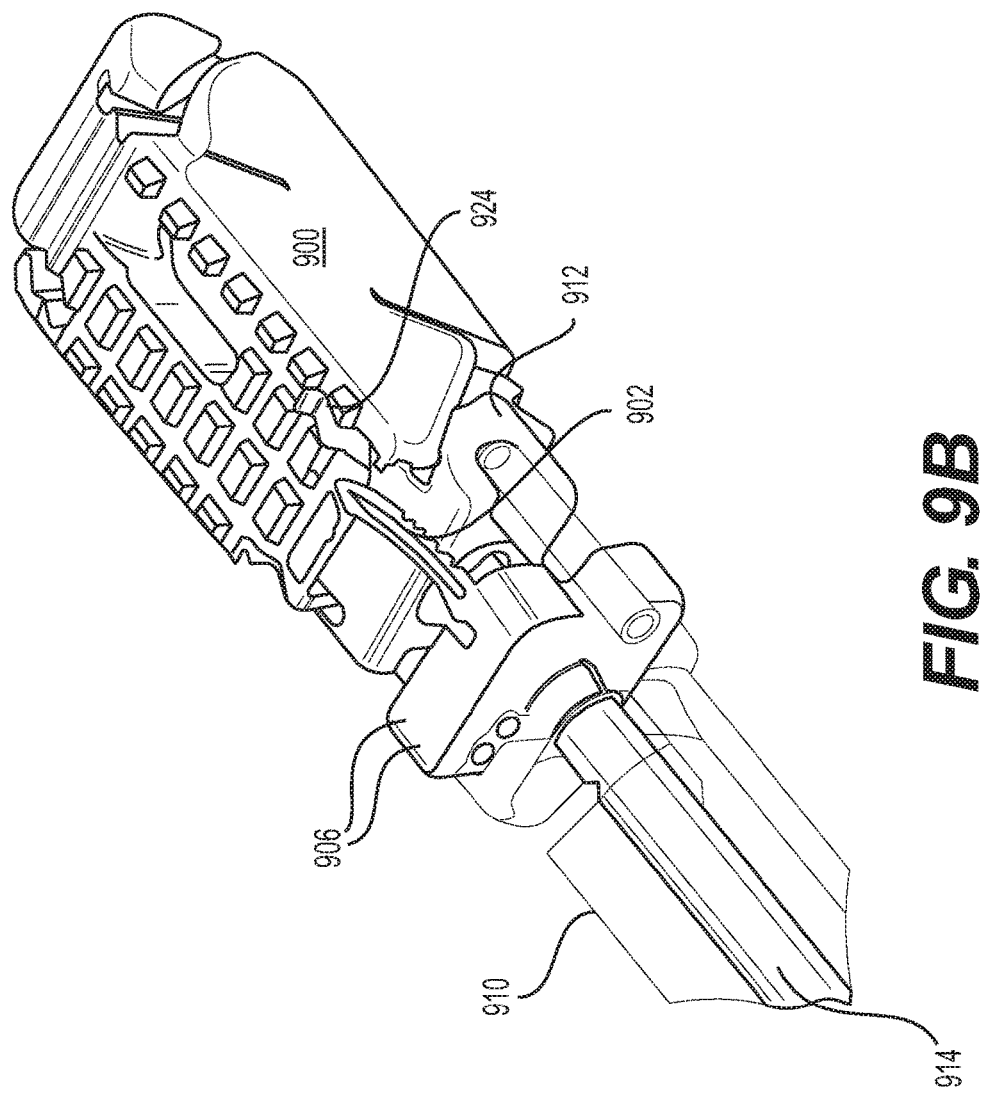

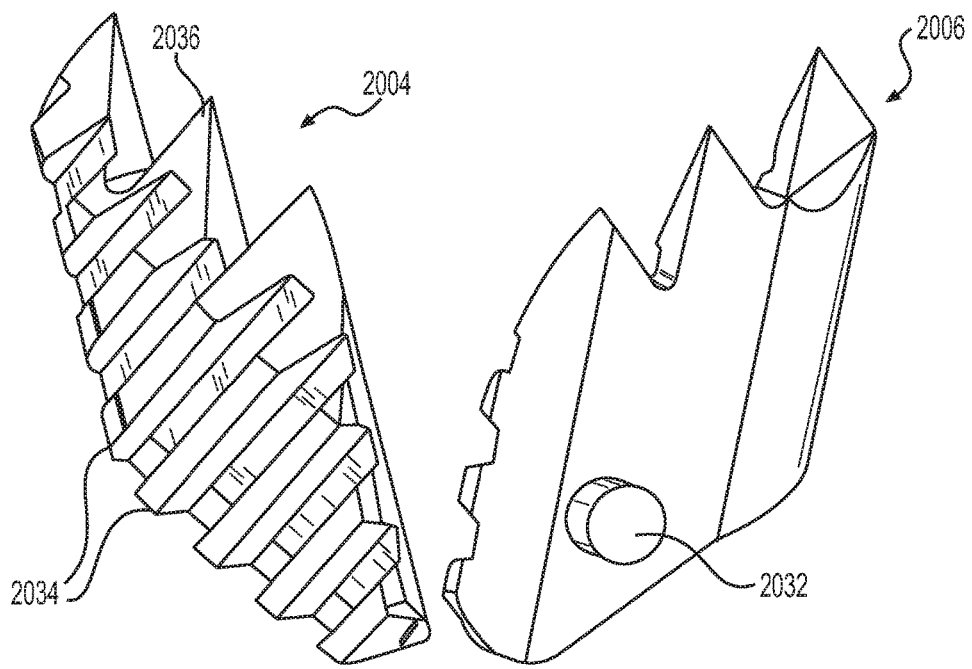
FIG. 15  FIG. 16
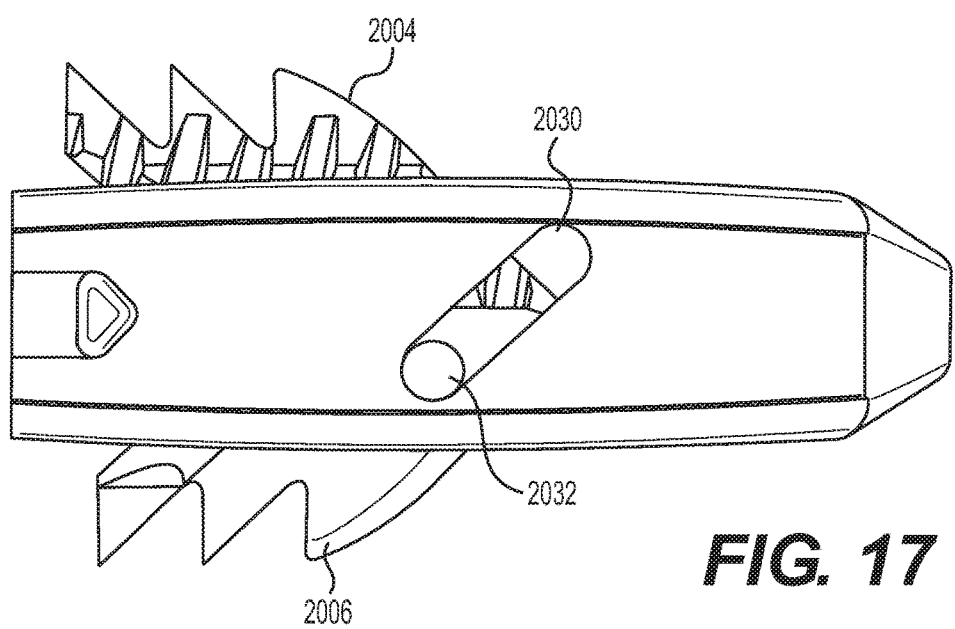
FIG. 17

DEVICE AND METHOD FOR DEPLOYMENT OF AN ANCHORING DEVICE FOR INTERVERTEBRAL SPINAL FUSION

CROSS-REFERENCE TO RELATED APPLICATIONS

This patent application is a continuation-in-part application of U.S. patent application Ser. No. 14/718,514 filed on May 21, 2015, which in incorporated in its entirety herein.

FIELD OF THE INVENTION

The present invention relates generally to intervertebral spacers for fusing adjacent vertebras, and more particularly to a device and methods for doing so.

BACKGROUND

Intervertebral spinal fusion is well known in the art. In the prior art, intervertebral spacer is implanted between two adjacent intervertebral bodies. The spacer allows a surgeon to deposit bone graft between the problem vertebras in order to fuse the vertebras together. To achieve proper fusion, the implanted spacer must be securely anchored between the vertebras such that there is little to no movement once implanted. Protrusions arranged on the superior and inferior surfaces of the spacer provides a means to stabilize the spacer between the vertebras. However, it has been discovered that spacers stabilized in this way may still move due to the stress exerted on the implanted spacer when the patient moves. Other commonly employed stabilizing techniques include pedicle screws and rods. In this technique, pedicle screws are independently screwed into two or three spine segments. A short rod is then used to connect the pedicle screws to prevent motion at the segments that are being fused. However, this technique is time consuming because the pedicle screws need to be independently screwed into the vertebras. It also requires the surgeon to make large/numerous incisions in the patient to insert the pedicle screws. Because of these deficiencies in the prior art, there exists a need to provide a more effective and efficient way of stabilizing adjacent vertebras in the field of intervertebral spinal fusion.

SUMMARY

For the purpose of the following description and the appended claims, "proximal" and its inflected forms are defined as the part, portion, section, etc., of an object that is closest to the person using that object.

For the purpose of the following description and the appended claims, "distal" and its inflected forms are defined as the part, portion, section, etc., of an object that is furthest away to the person using that object.

The present invention provides a way to stabilize adjacent vertebras without some of the deficiencies of the prior art discussed above. In the illustrative embodiment of the present invention, a spacer is provide with an upper guide and a lower guide. The upper and lower guides are adapted to guide the simultaneous deployment of a respective upper anchor and lower anchor of an anchoring device when force is applied thereto. More precisely, force is simultaneously applied to a proximal portion of the upper and lower anchors. The force simultaneously deploys the upper and lower anchors into their respective intervertebral bodies. The upper and lower anchors are constructed and dimensioned in such a way to pierce and penetrate into their respective vertebras. The combination of the anchors and the protrusions arranged on the surfaces of the spacer provides additional stabilization of the implanted spacer. These advantages of the present invention will be apparent from the following disclosure and the appended claims.

BRIEF DESCRIPTION OF THE DRAWINGS

FIG. 6A depicts the implantation instrument of FIG. 5A having deployed the anchors of FIG. 4A;

FIG. 9A-9H depict an upper anchor and a lower anchor arranged on a drive plate in accordance with an alternative embodiment of the present invention.

FIGS. 15 and 16 depict the anchors of the implant illustrated in FIG. 11.

FIG. 17 depicts a lateral view of the implant according to one embodiment of the present invention.

DETAILED DESCRIPTION

Figure 1A:
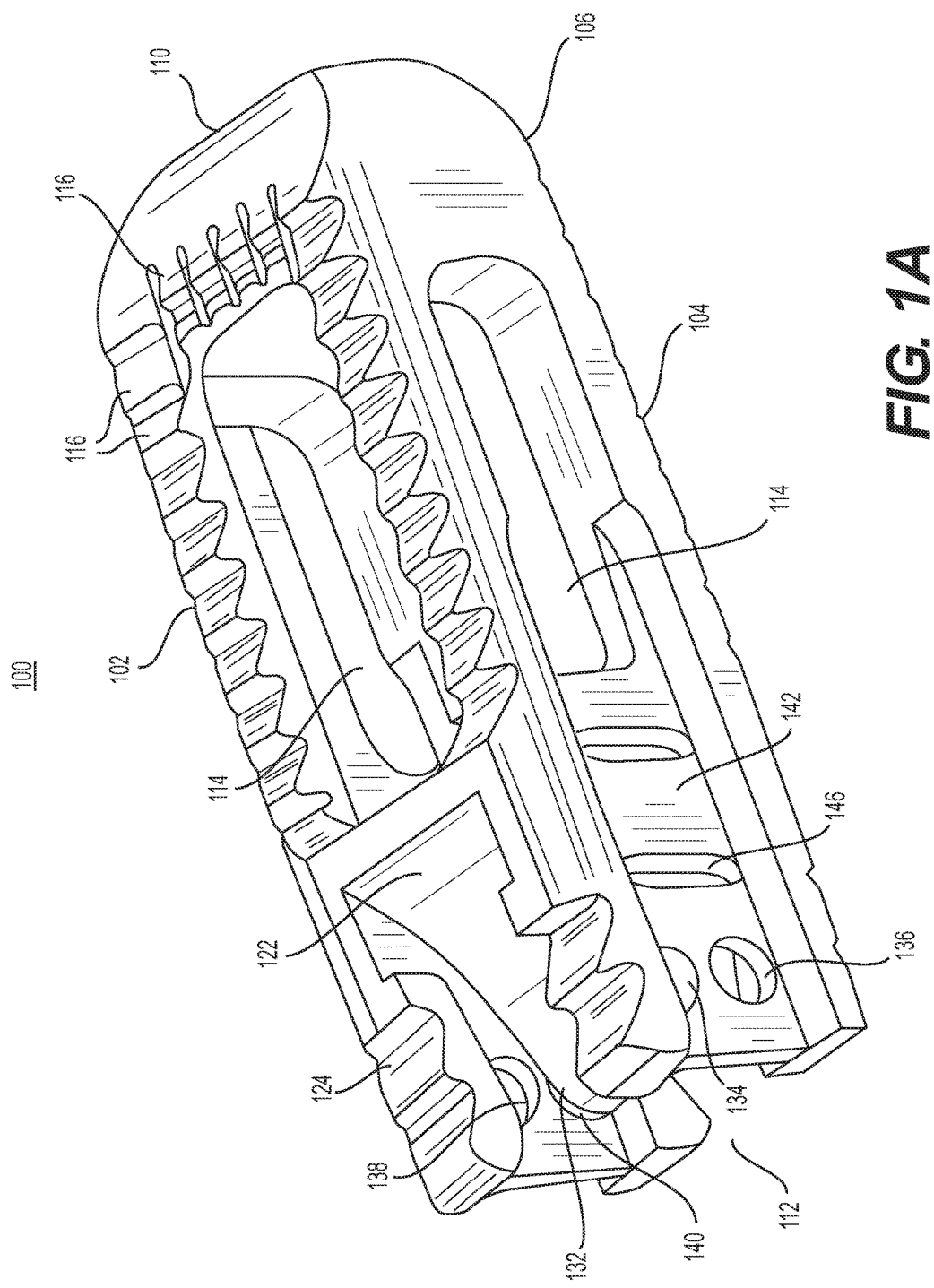
FIG. 1A depicts a perspective view of an intervertebral spacer in accordance with an illustrative embodiment of the present invention.
Figure 1B:
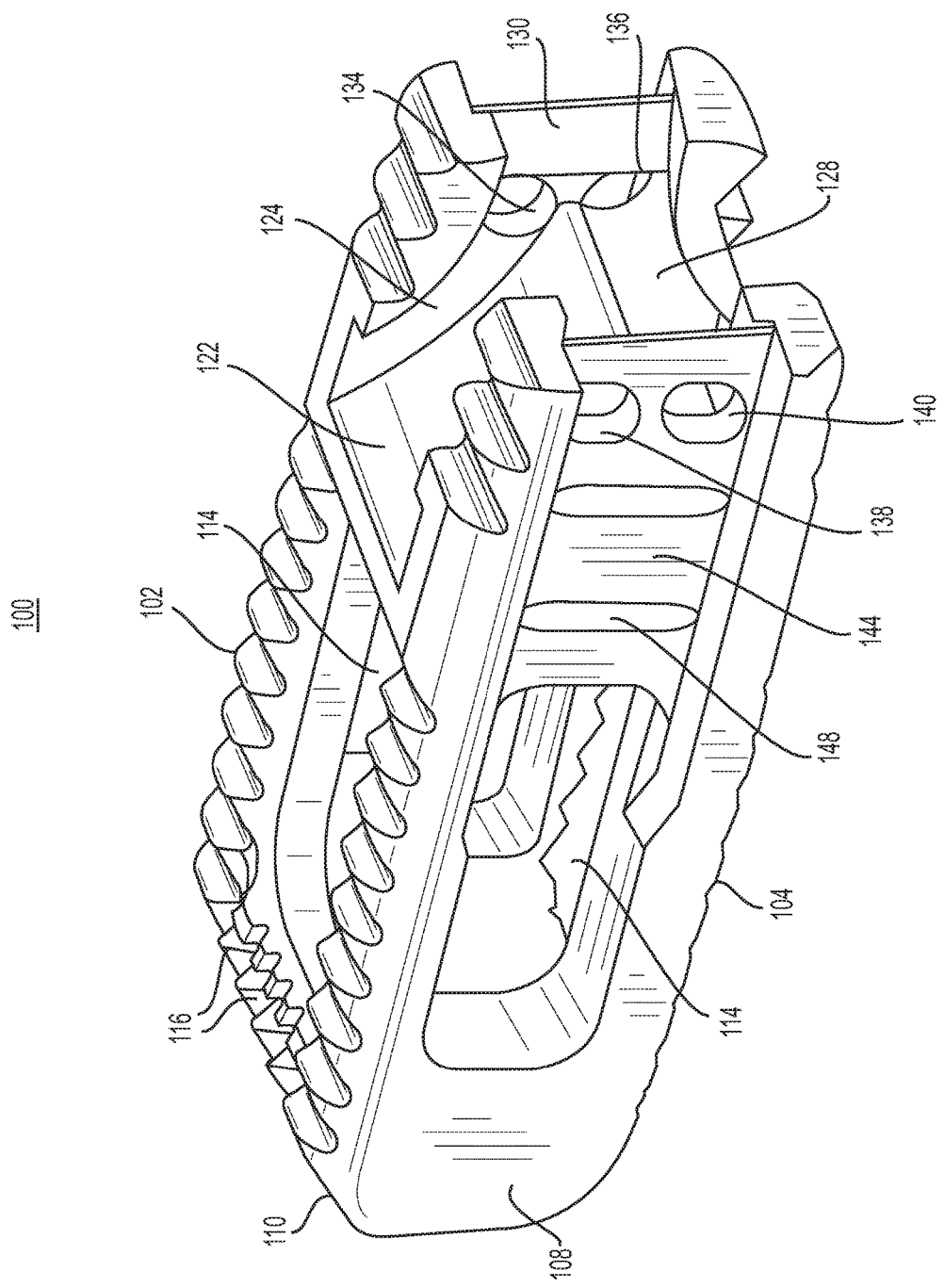
FIG. 1B depicts another perspective view of the intervertebral spacer of FIG. 1A.

FIGS. 1A and 1B depict perspective views of intervertebral spacer 100 in accordance with an illustrative embodiment of the present invention. Spacer 100 generally has a rectangular shape, but the present invention is not limited to such a shape. Spacer 100 can have any shape, size, or combination thereof to meet the needs of a spinal fusion candidate.

As depicted in FIGS. 1A and 1B, spacer 100 comprises superior surface 102, inferior surface 104, lateral surfaces 106 and 108, distal portion 110, and proximal portion 112. Inferior surface 104 is a mirror image of superior surface 102 and lateral surface 108 is a mirror image of lateral surface 106. Spacer 100 is preferably formed from titanium alloy but other biocompatible materials (e.g., polyetheretherketone (PEEK), other surgical grade metals, alloys, or a combination thereof) can also be used to form spacer 100.

Beginning at distal portion 110, spacer 100 is constructed to have a tapered end that narrows towards the distal most end. This design helps facilitate easier entry of spacer 100 into the narrow disc space arranged between two adjacent vertebral bodies.

Figure 2A:
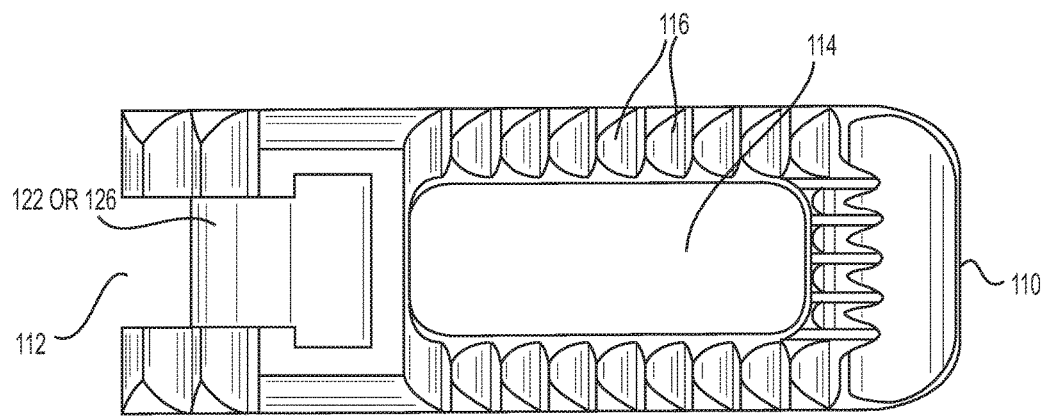
FIG. 2A depicts a top view of the intervertebral spacer of FIGS. 1A and 1B.
Figure 2B:
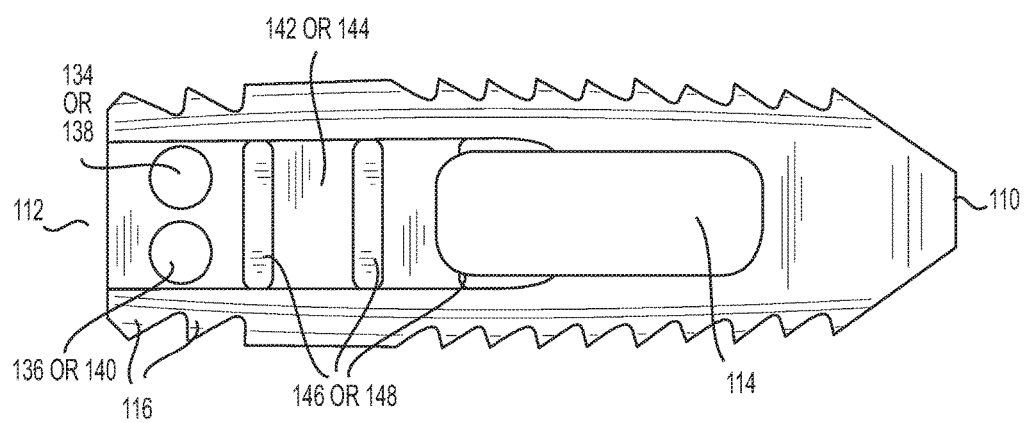
FIG. 2B depicts a side view of the intervertebral spacer of FIGS. 1A and 1B.

To fuse the adjacent vertebras together, bone graft is used. For this purpose, the body of spacer 100 is provided with through-hole 114. The through-hole extends through the center of surfaces 102, 104, 106, and 108 and is adapted to receive the bone graft for fusing the adjacent vertebras. In the illustrative embodiment, through-hole 114 generally has a rectangular shape. However, those skilled in the art will appreciate after reading this disclosure that through-hole 114 can have any shape, size, or a combination thereof. As further depicted in FIGS. 1A and 1B, surfaces 102 and 104 are provided with a plurality of protrusions or teeth 116 to help prevent spacer 100 from expulsion after being implanted between the adjacent vertebras. It will be appreciated by those skilled in the art, after reading this disclosure, that teeth 116 can be angled in any number of degrees (e.g., 45°, 90°, etc.) and can have any number of orientations without departing from the scope of the present invention. Through-hole 114 and teeth 116 can be seen more clearly in FIGS. 2A and 2B.

Turning now to proximal portion 112, upper and lower guides are provided to respectively guide the deployment of upper anchor 118 and lower anchor 120 into their respective vertebral bodies. The upper and lower anchors will be discussed in more detail below, with respect to FIGS. 3A and 3B. In the illustrative embodiment, the upper guide is characterized by an upper inclined surface 122 (e.g., a curvilinear surface, etc.) and an upper pair of oppositely positioned lateral recesses 124. Because the lower guide is a mirror image of the upper guide, the lower guide is also characterized by a lower inclined surface 126 and a lower pair of oppositely positioned lateral recesses 128. The upper and lower pair of lateral recesses 124 and 128 are dimensioned to respectively complement the arc, curvature, etc., of the upper and lower anchors. An advantage of recesses 124 and 128 is that they ensure that their respective anchors maintain a desired trajectory when impacted by an anchor driver. The recesses 124 and 128 also prevent their respective anchors from egressing out of spacer 100 when impacted by the anchor driver. These features and their advantages will be discussed in more detail below, with reference to FIGS. 4A and 4B.

Proximal portion 112 also comprises a pair of oppositely positioned lateral chamfers 130 and 132. Each of the lateral chamfers has a sloping edge and is positioned proximally to their respective locking recesses 134, 136, 138, and 140. As will be described in more detail below, with reference to FIGS. 6A-6D, the chamfer-recess combination is a mechanism that allows upper anchor 118 and lower anchor 120 to be locked to spacer 100 after deployment. It will be appreciated by those skilled in the art, after reading this disclosure, that locking recesses 134, 136, 138, 140 could be detents in some embodiments and through-holes in other embodiments.

Proximal portion 112 further comprises lateral surfaces 142 and 144 that are respectively constructed with gripper recesses 146 and 148. The gripper recesses are dimensioned and arranged to receive corresponding ribs of an implantation instrument employed by a surgeon. The ribs are adapted to fit squarely into their corresponding recesses so that spacer 100 can be securely gripped by the surgeon. It should be noted that gripping the spacer with an implantation instrument serves at least two purposes. First, it enables the surgeon to more easily orient spacer 100 in a desired position within the narrow disc space of the adjacent vertebras. Secondly, it prevents spacer 100 from coming free from the implantation instrument while the surgeon is impacting the upper and lower anchors with an anchor driver. Although each of the lateral surfaces is depicted as having three gripping recesses, it will be appreciated by those skilled in the art that each of the lateral surfaces can have more or less gripper recesses than depicted. This feature of the present invention will be described in more detail below, with reference to FIGS. 5A-5D.

Figure 3A:
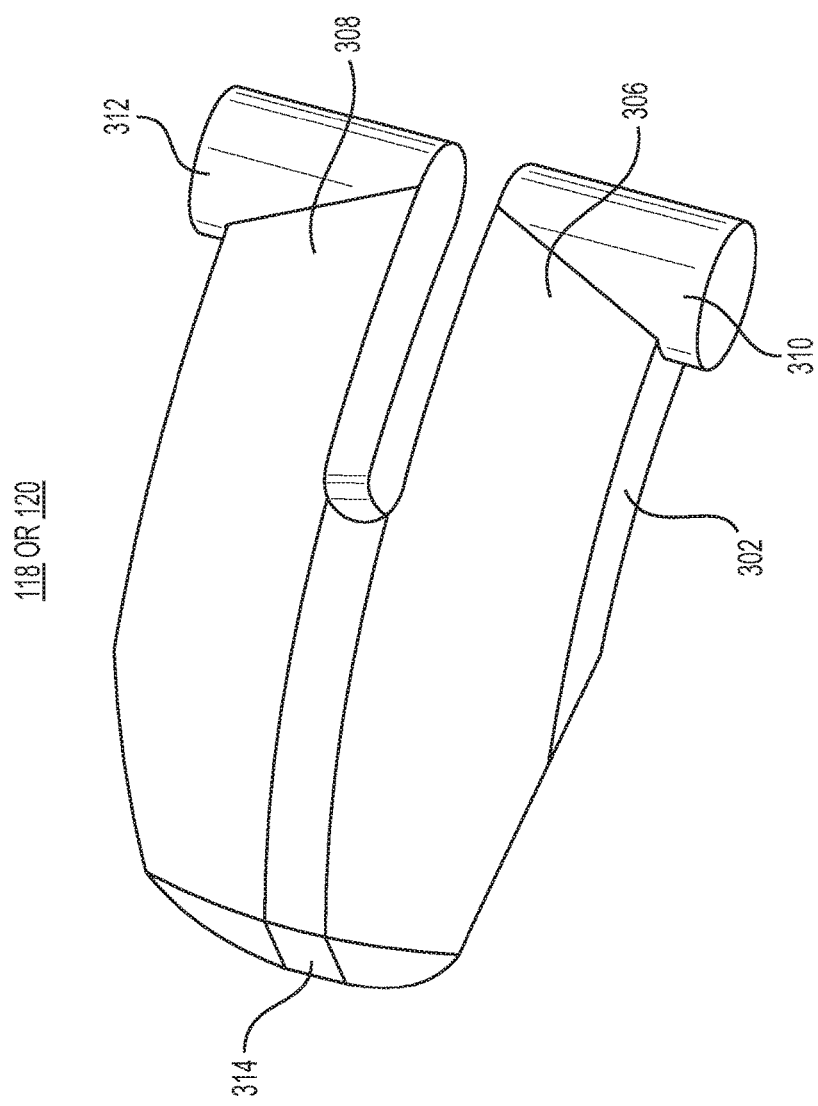
FIG. 3A depicts one side of an anchor in accordance with an illustrative embodiment of the present invention.
Figure 3B:
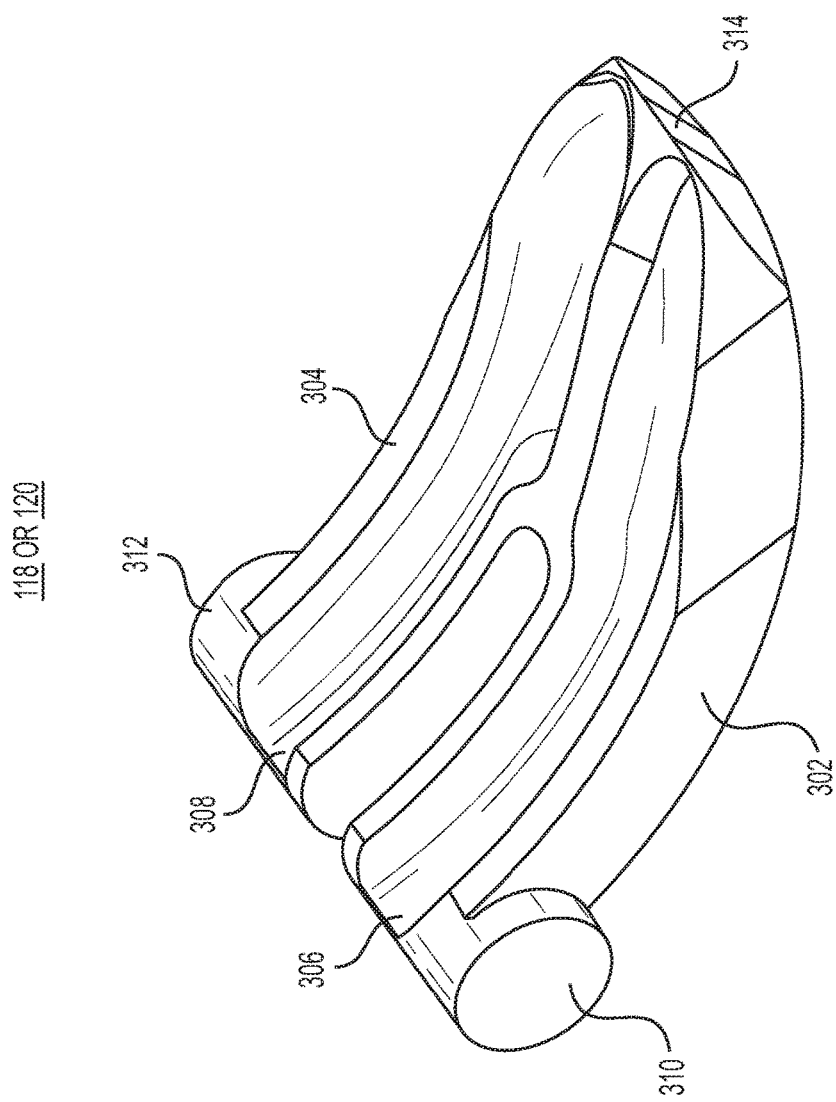
FIG. 3B depicts the other side of the anchor of FIG. 3A.

FIGS. 3A and 3B are perspective views of an anchor in accordance with an illustrative embodiment of the present invention. Since upper anchor 118 and lower anchor 120 have substantially the same physical and functional characteristics, thus being interchangeable, the following discussion of FIGS. 3A and 3B will use the word "anchor" to describe both the upper and lower anchors. Further, it should be noted that upper anchor 118 and lower anchor 120 (whether formed as independent pieces or as a single unitary piece) collectively define an anchoring device.

FIG. 3A depicts the surface of an anchor that is adapted to slide along an inclined surface of a guide (e.g., upper inclined surface 122 or lower inclined surface 126). In the illustrative embodiment, the anchor is constructed to have a curved or semi-curved surface that is contoured to be substantially the same as the inclined surface of the guide it slides on. The surface of the anchor is preferably smooth throughout its length in order to reduce the amount of friction drag produced when the surface slides along the inclined surface.

The anchor also comprises a pair of oppositely positioned lateral sides 302 and 304, which are adapted to slide into their respective lateral recesses (e.g., upper lateral recesses 124 or lower lateral recesses 128). The anchor is also constructed with a pair of flexible prongs 306 and 308, which respectively comprises lateral projections 310 and 312. The flexible prongs and lateral projections work in cooperation to lock the anchor to spacer 100 in a deployed position. The lateral sides, flexible prongs, and lateral projections of the anchor are also depicted in FIG. 3B.

To enable the anchor to penetrate a vertebral body, distal portion 314 of the anchor is tapered to form an edge. Since the anchor is made of titanium alloy, the distal portion of the anchor is sufficiently strong to pierce and penetrate through the endplate of the vertebral body. Although the anchor is preferably formed from titanium alloy, other biocompatible materials (e.g., polyetheretherketone (PEEK), other surgical grade metals, alloys, or a combination thereof) can be used to form the anchor.

It will be clear to those skilled in the art that the foregoing discussion of FIGS. 3A and 3B applies to both upper anchor 118 and lower anchor 120.

Figure 4A:
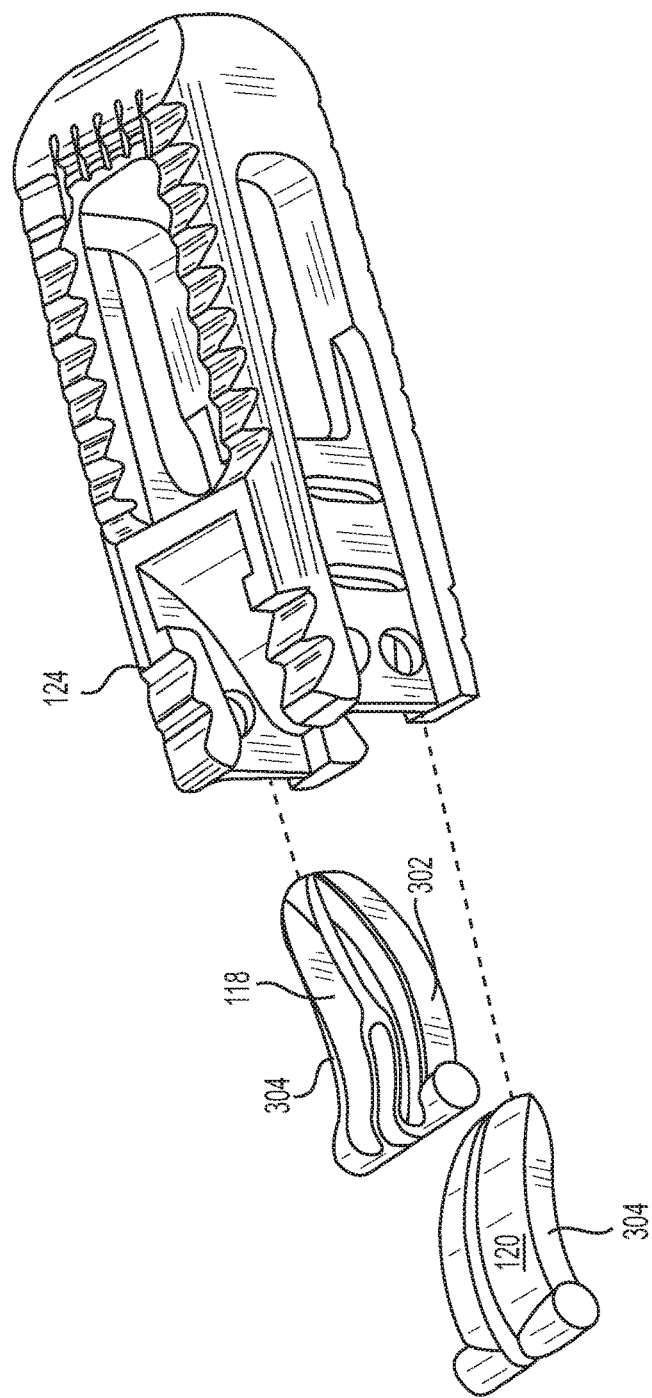
FIG. 4A depicts two anchors being loaded into the intervertebral spacer of FIGS. 1A and 1B.
Figure 4B:
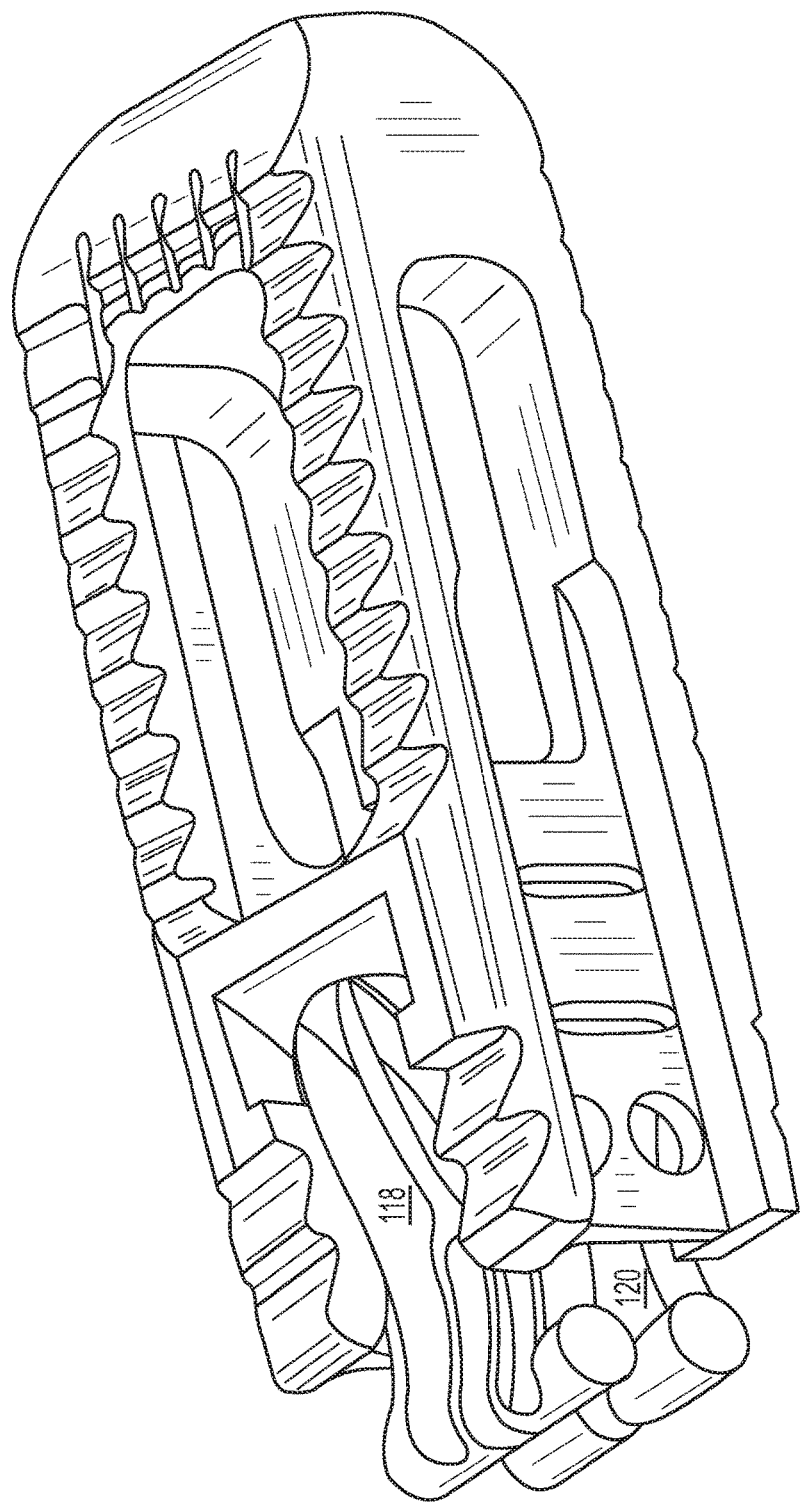
FIG. 4B depicts the two anchors of FIG. 4A loaded into the intervertebral spacer of FIGS. 1A and 1B, the two anchors being in an undeployed state.

FIG. 4A depicts upper anchor 118 and lower anchor 120 being loaded into spacer 100. As discussed above, the upper guide of spacer 100 has an upper pair of oppositely positioned lateral recesses 124. Each lateral recess 124 is adapted to receive a respective one of lateral sides 302 and 304 of upper anchor 118. Similarly, the lower guide of spacer 100 has a lower pair of oppositely positioned lateral recesses 128 (shown more clearly in FIG. 1B). Each lateral recess 128 is adapted to receive a respective one of lateral sides 302 and 304 of lower anchor 120. Turning now to FIG. 4B, this figure depicts spacer 100 loaded with the upper and lower anchors. In FIG. 4B, upper anchor 118 and lower anchor 120 are in an undeployed state and are disposed entirely within spacer 100. That is, no part of upper anchor 118 and lower anchor 120 extend beyond the profile of teeth 116 arranged on spacer 100. In the loaded/undeployed state, spacer 100 is ready to be gripped by an implantation instrument for simultaneous deployment into their respective intervertebral bodies.

Figure 5A:
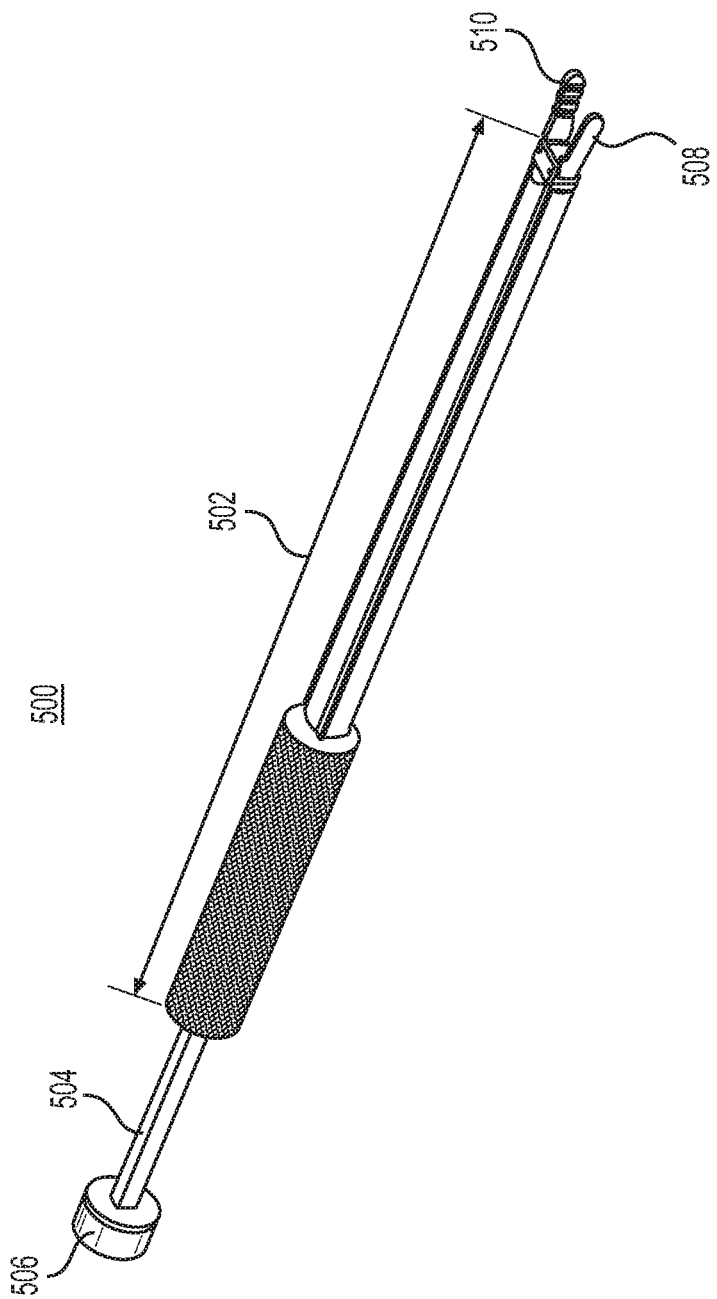
FIG. 5A depicts a perspective view of an implantation instrument in accordance with an illustrative embodiment of the present invention.

FIG. 5A is a perspective view of implantation instrument 500, which comprises, inter alia, housing 502, anchor driver 504, handle 506, and a pair of oppositely positioned grippers 508 and 510. As will be discussed in more detail below, with reference to FIGS. 5B-5D, anchor driver 504 can be advanced forwards or retracted backwards via handle 506 to respectively grip or release spacer 100.

Figure 5B:
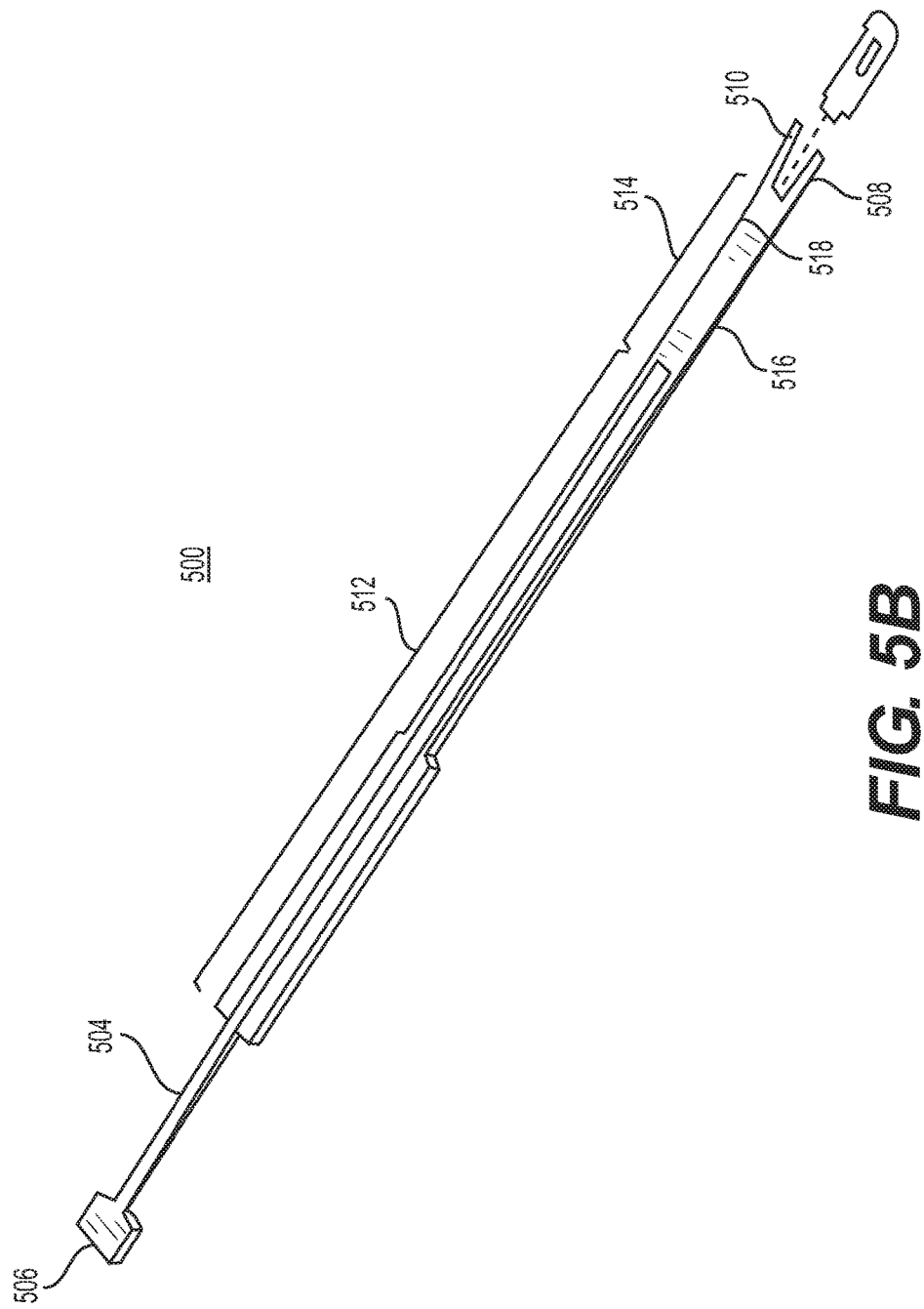
FIG. 5B depicts a cross-sectional view of the implantation instrument of FIG. 5A, the cross-sectional view depicting a narrower section and a wider section of the implantation instrument.

FIG. 5B is a cross-sectional view of the implantation instrument of FIG. 5A. As shown in this view, housing 502 is divided into two sections—namely, a narrower section 512 and a wider section 514. Anchor driver 504 is constructed to fit squarely into narrower section 512 with little or no lateral and radial movement, while the area of wider section 514 is dimensioned to accommodate the width of anchor driver 504 and a pair of adjacently positioned, oppositely bowed leaf springs 516 and 518.

In the configuration depicted in FIG. 5B, anchor driver 504 can be advanced forwards towards leaf springs 516 and 518 via handle 506. As the forward advancement causes anchor driver 504 to be wedged between leaf springs 516 and 518, their respective grippers 508 and 510 will begin to simultaneously pivot inward to clamp onto the lateral surfaces of spacer 100.

Figure 5C:
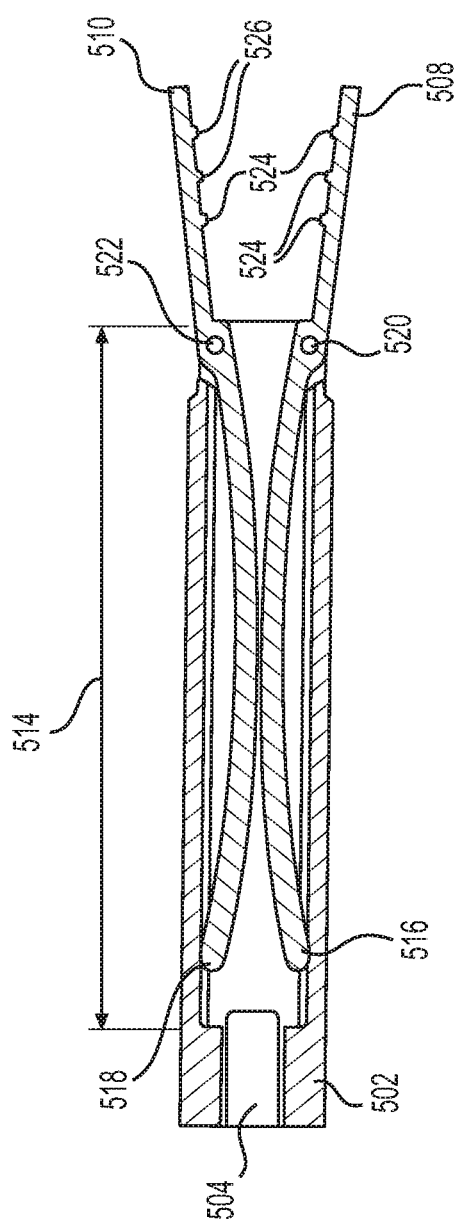
FIG. 5C depicts an exploded, cross-sectional view of the wider section of the implantation instrument of FIG. 5A.

More precisely, and with reference to FIG. 5C, the forward advancement of anchor driver 504 causes gripper 508 to pivot inwardly about pivot point 520. This pivot action is a result of leaf spring 516 being compressed outwards towards the wall of housing 502 as anchor driver 504 engages the bowed portion of leaf spring 516. As gripper 508 pivots inwards, ribs 524 engage their respective gripper recess 146 (depicted in FIG. 1A) arranged on spacer 100. Likewise, gripper 510 will pivot inwardly about pivot point 522 in response to the forward advancement of the driver, resulting in ribs 526 engaging their respective gripper recess 148 (depicted in FIG. 1B). By means of the foregoing, spacer 100 can be securely gripped by implantation instrument 500, as depicted in FIG. 5D.

Figure 5D:
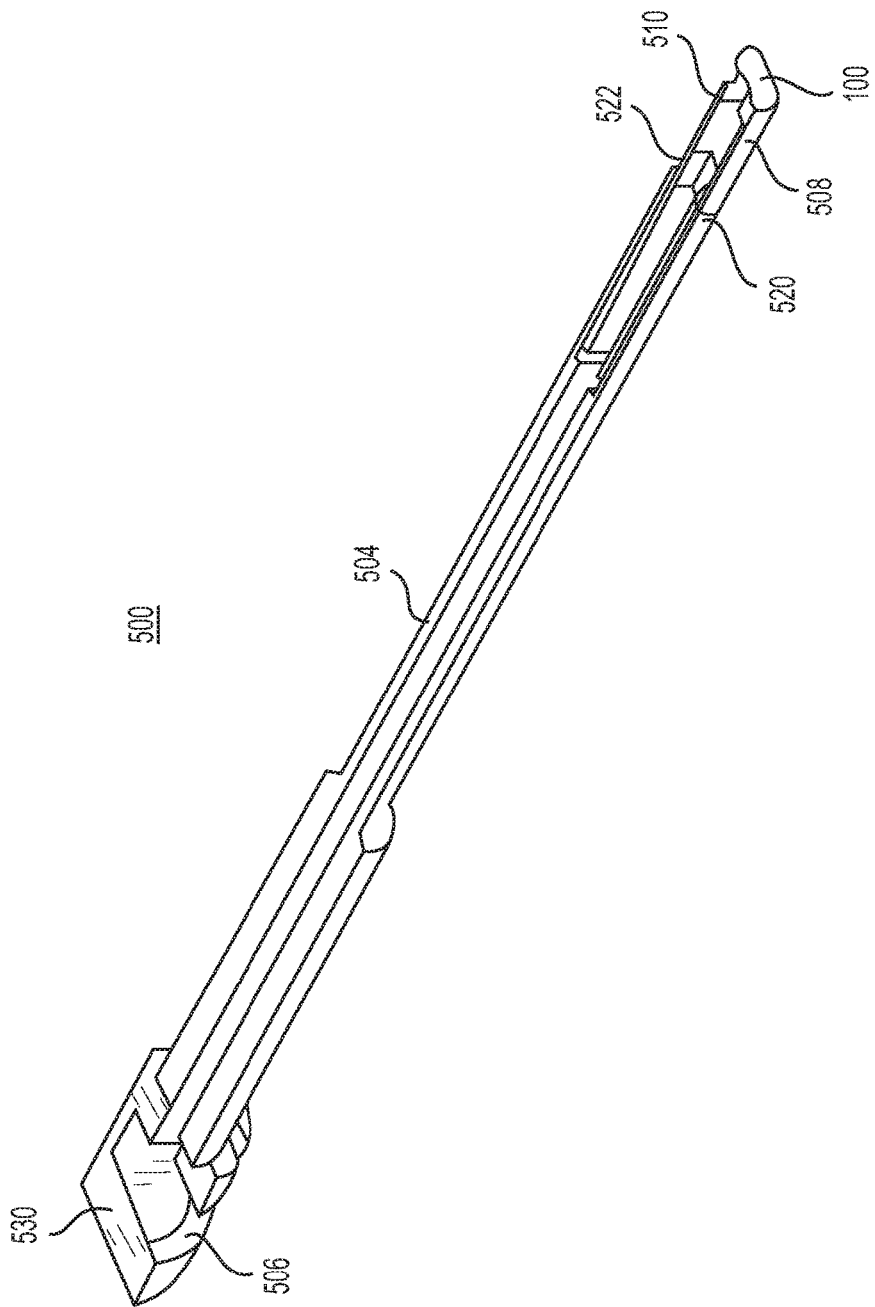
FIG. 5D depicts a cross-sectional view of the implantation instrument gripping the lateral surfaces of the intervertebral spacer of FIGS. 1A and 1B.

As depicted in FIG. 5D, the head of anchor driver 504 stops at or slightly before the distal end of housing 502 after gripping spacer 100. While spacer 100 is being gripped by implantation instrument 500, spacer 100 is positioned within the narrow disc space between adjacent vertebras. Continuing to grip spacer 100 with implantation instrument 500, the surgeon removes cap 530 and is now ready to impact handle 506 with a weighted object (e.g., hammer, mallet, etc.). In accordance with the illustrative embodiment, cap 530 has two functionalities. First, cap 530 when attached to handle 506 disallows forward movement of anchor driver 504 past a certain point—namely, the distal end of housing 502. Secondly, cap 530 prevents inadvertent deployment of upper anchor 118 and lower anchor 120 during positioning of spacer 100 within the adjacent vertebral bodies.

When the surgeon impacts handle 506 with a weighted object, anchor driver 504 is driven forwards into the proximal portion of upper anchor 118 and lower anchor 120, thereby simultaneously deploying the anchors into their respective vertebras. The surgeon may impact handle 506 one or more times so that the anchors reach a desired depth within their vertebras, and so that the anchors engage the locking feature of the present invention described in more detail below. Once upper anchor 118 and lower anchor 120 is locked to spacer 100 in the deployed position, the surgeon can retract anchor driver 502 so that leaf springs 516 and 518 can return to their relaxed state. While returning to their relaxed state, grippers 508 and 510 will begin to pivot outwardly to disengage from their gripper recesses, thereby releasing spacer 100.

Figure 6B:
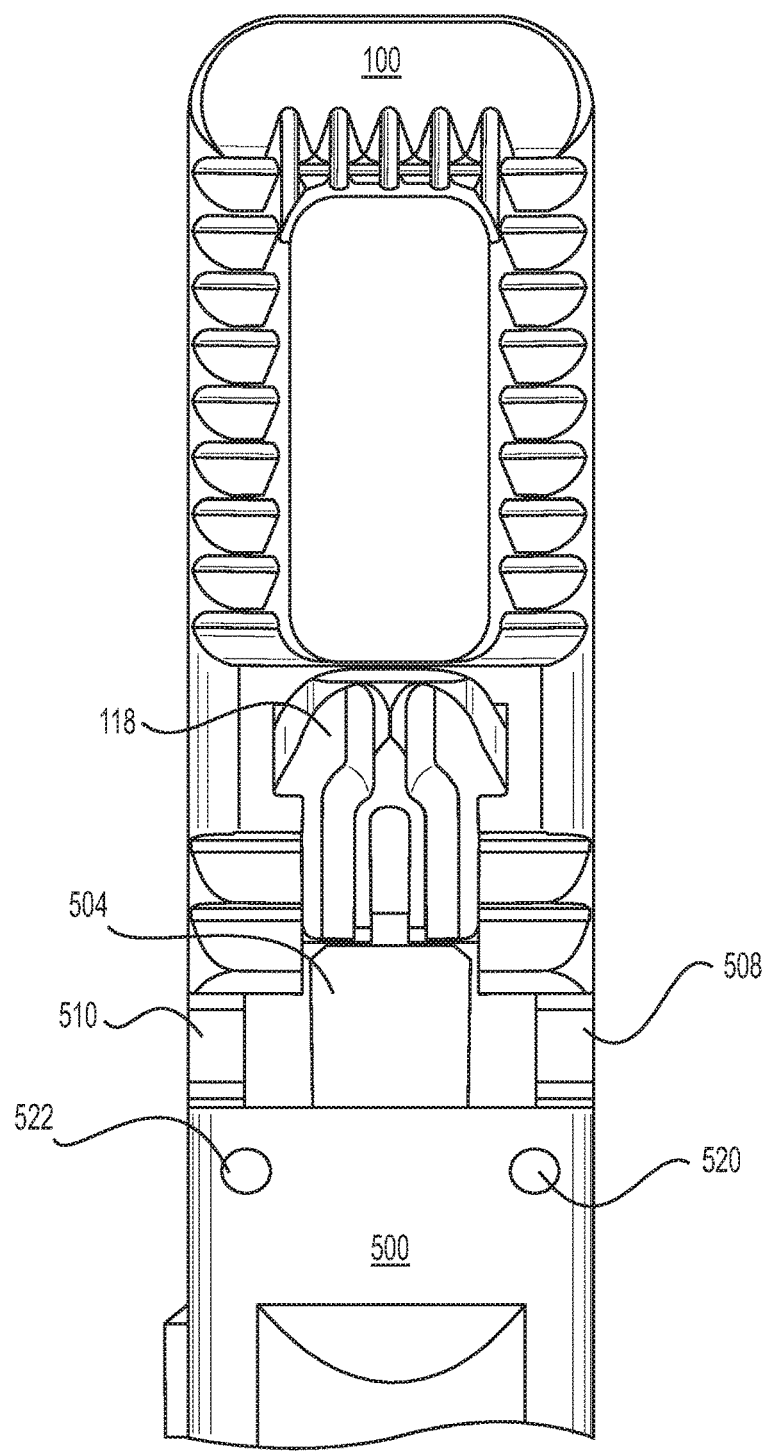
FIG. 6B depicts an exploded, top view of the deployed anchors of FIG. 6A.
Figure 6C:
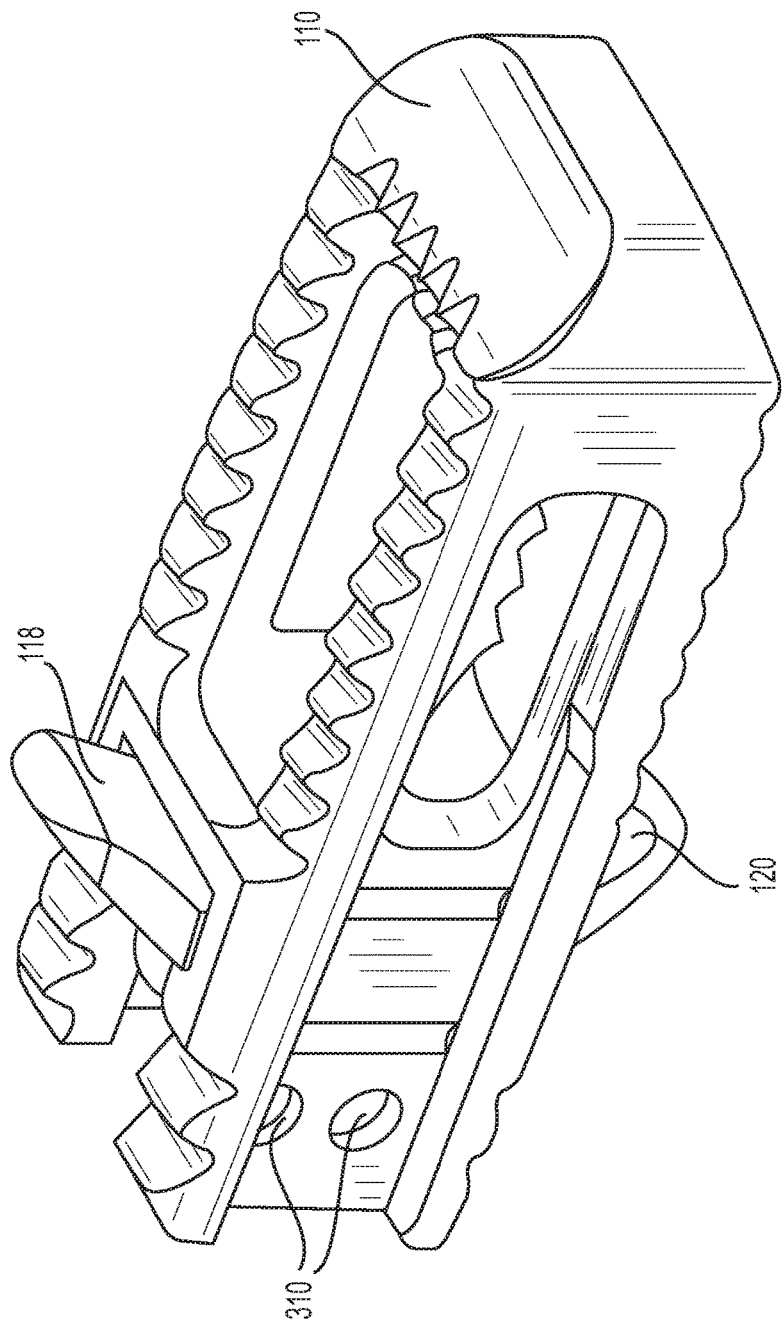
FIGS. 6C and 6D depict an exploded, perspective view of the deployed anchors of FIG. 6A.
Figure 6D:
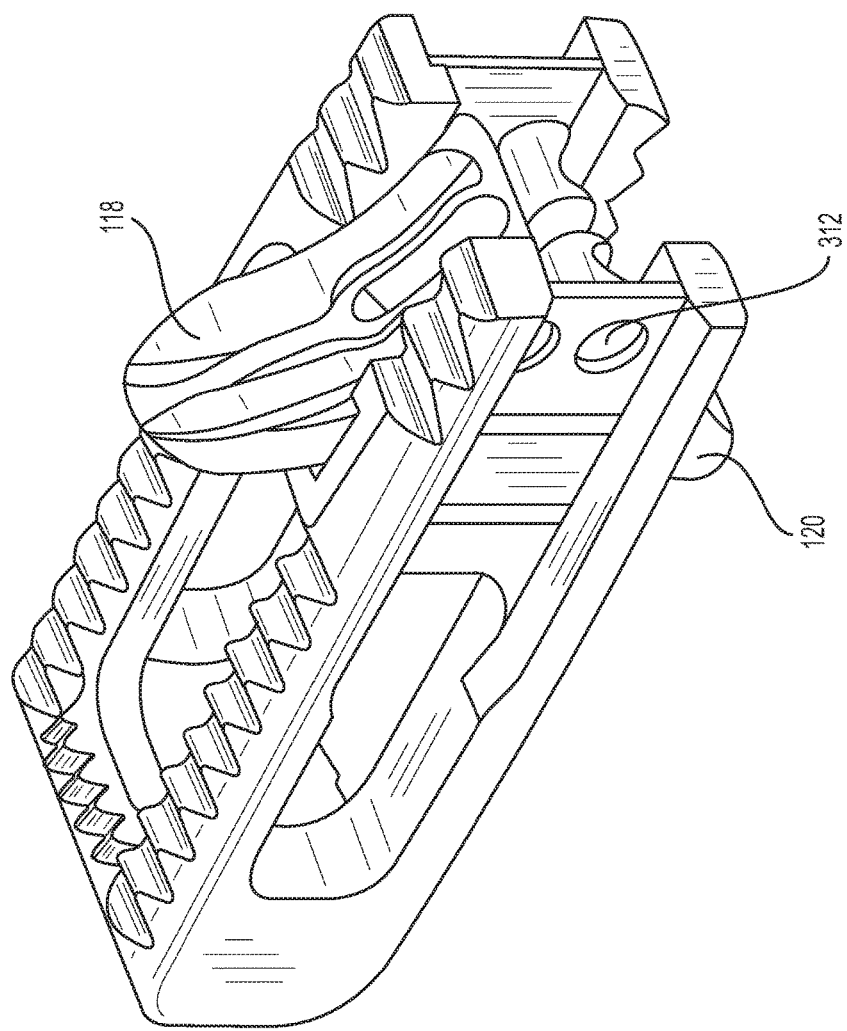

FIG. 6A depicts a perspective view of implantation instrument 500 in which driver anchor 504 has simultaneously deployed upper anchor 118 and lower anchor 120. As discussed above, the head of anchor driver 504 is simultaneously driven into the proximal portion of upper anchor 118 and lower anchor 120 as the surgeon impacts handle 506. This causes both the upper anchor 118 and lower anchor 120 to independently slide along the upper inclined surface 122 and lower inclined surface 126, respectively. The upper and lower inclined surfaces respectively press against the surface of the upper and lower anchors (i.e., the surface depicted in FIG. 3A) to deploy the anchors into their respective vertebral bodies. FIGS. 6B-6D depict upper anchor 118 and lower anchor 120 simultaneously deployed after being impacted by anchor driver 504. As shown in these figures, the distal ends of upper anchor 118 and lower anchor 120 in the deployed state are radially extended outside of spacer 100. That is, the distal ends of upper anchor 118 and lower anchor 120 extend past the height of teeth 116 of spacer 100 after being deployed.

From the foregoing discussion, it will be clear to those skilled in the art that upper anchor 118 and lower anchor 120 are separate elements that slide independently of each other along their respective upper and lower guides. It will also be clear from the foregoing discussion that an advantage of using the upper and lower anchors of the present invention is that they provide additional anchorage for stabilizing a spacer. In other words, not only is the spacer anchored to the intervertebral bodies via its teeth, the spacer is also provided with additional anchorage by the upper and lower anchors, since they extend past the profile of the teeth and therefore penetrating deeper into the intervertebral bodies.

Returning to FIGS. 6C and 6D, these figures depict upper anchor 118 and lower anchor 120 locked to spacer 100 in a deployed position. Since upper anchor 118 and lower anchor 120 are locked to spacer 100 in substantially the same way, the following discussion of FIGS. 6C and 6D will use the word "anchor" to describe both the upper and lower anchors.

As the anchor is impacted by driver 504, lateral projections 310 and 312 will respectively engage the sloping edge of lateral chamfers 130 and 132. Lateral chamfers 130 and 132 are depicted in the figures as being arranged proximally to locking recesses 134, 136, 138, and 140 of spacer 100. The pressure and force of the impact causes flexible prongs 306 and 308 to flex laterally inwardly. As lateral projections 310 and 312 past their respective lateral chamfers, flexible prongs 306 and 308 will return to a relaxed state, thereby causing lateral projections 310 and 312 to laterally extend into their corresponding locking recess 134, 136, 138, and 140. This locking feature of the present invention prevents the anchors from disengaging from spacer 100 after being deployed into the vertebral bodies.

Figure 7A:
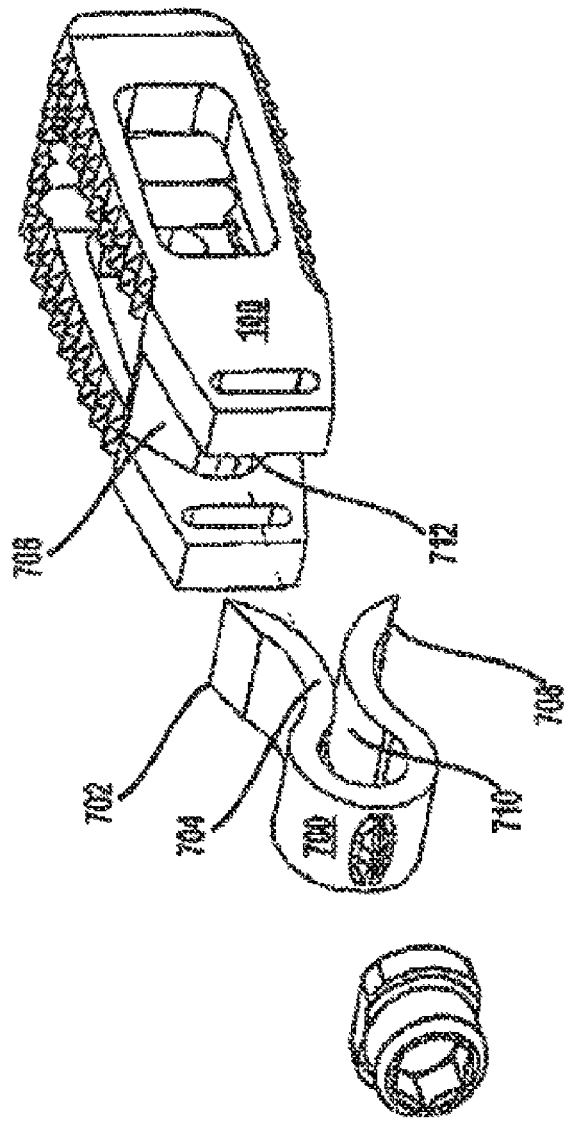
FIG. 7A-7C depict a spacer and anchor in accordance with an alternative embodiment of the present invention, wherein the upper and lower anchors of the anchoring device form a single, unitary piece.
Figure 7B:
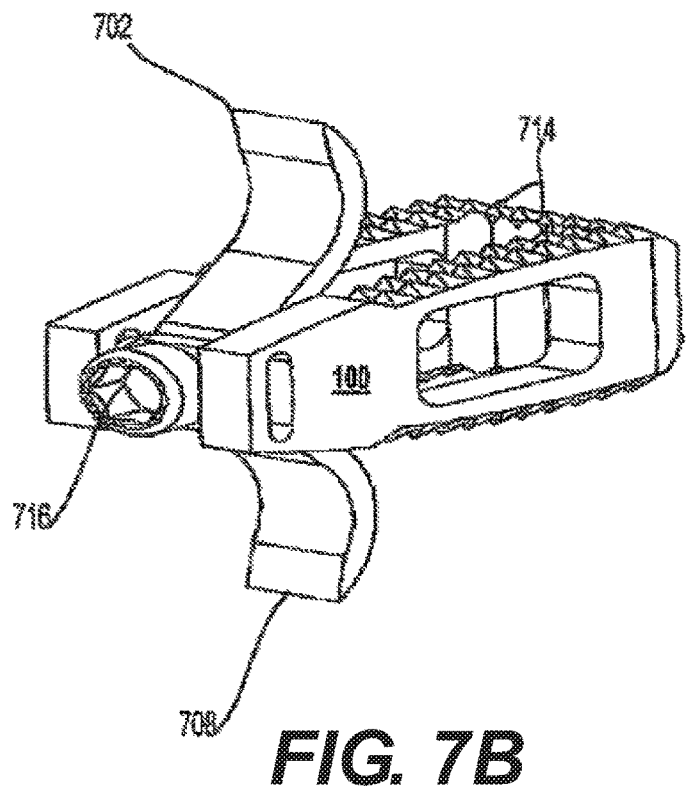
Figure 7C:
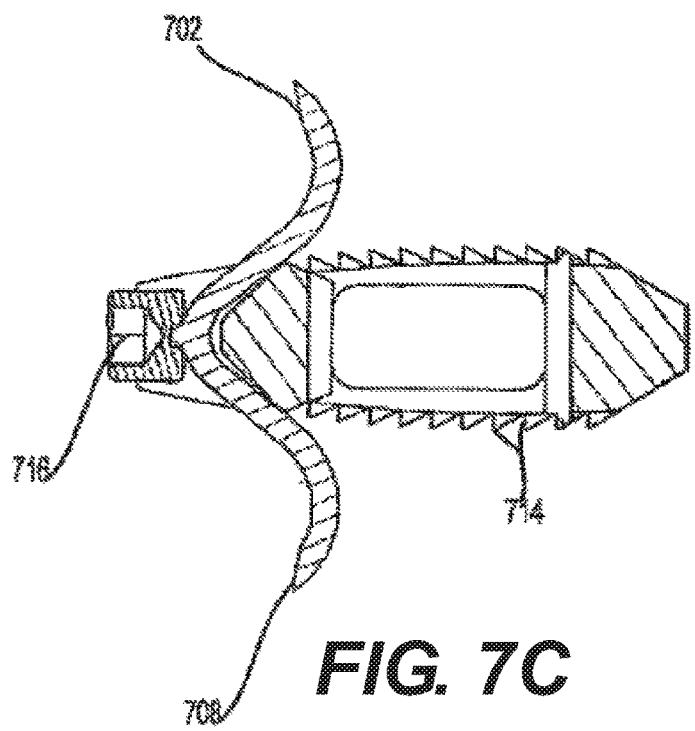

It will be clear to those skilled in the art, after reading this disclosure that numerous modification can be made to the illustrative embodiment without departing from the scope of the invention. For example, in one alternative embodiment, upper anchor 118 and lower anchor 120 can be constructed as a single unitary piece. FIGS. 7A-7C depict such an anchoring device.

As depicted in FIG. 7A, upper anchor 702 of anchoring device 700 comprises underside 704 that is adapted to press against upper inclined surface 706 of the upper guide arranged on spacer 100. Similarly, lower anchor 708 of anchoring device 700 comprises underside 710 that is adapted to press against lower inclined surface 712 of the lower guide arranged on spacer 100. As anchoring device 700 is advanced forwards, pressure causes the undersides to press against their respective inclined surfaces, which guides upper anchor 702 and lower anchor 708 to radially and simultaneously deploy into their respective vertebral bodies. As depicted in FIGS. 7B and 7C, upper anchor 702 and lower anchor 708 extend past the profile of teeth 714 to provide additional anchorage. Once the upper and lower anchors have been simultaneously deployed into their vertebra, locking cap 716 can be used to lock the anchors in their deployed position. Specifically, locking cap 716 is adapted to press the proximal end of anchoring device 700 to lock the anchoring device to spacer 100.

Figure 8A:
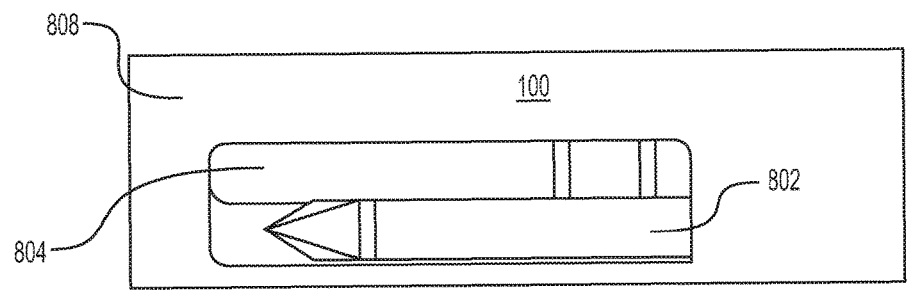
FIG. 8A-8C depict a spacer and anchor in accordance with an alternative embodiment of the present invention, wherein the upper and lower anchors of the anchoring device are disposed entirely within the spacer.
Figure 8B:
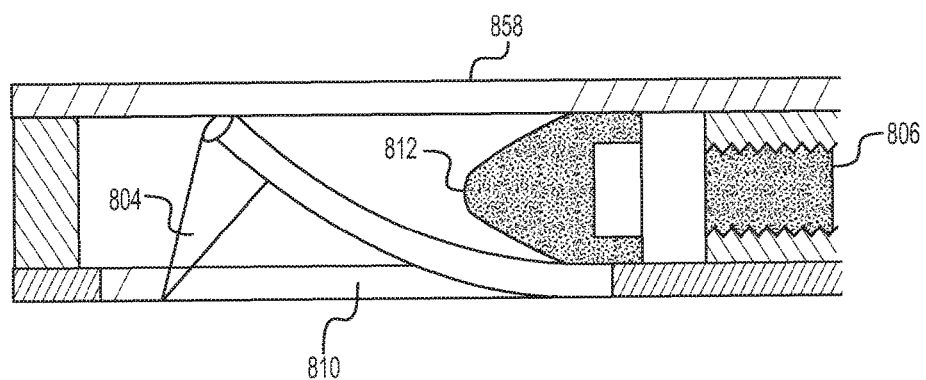
Figure 8C:
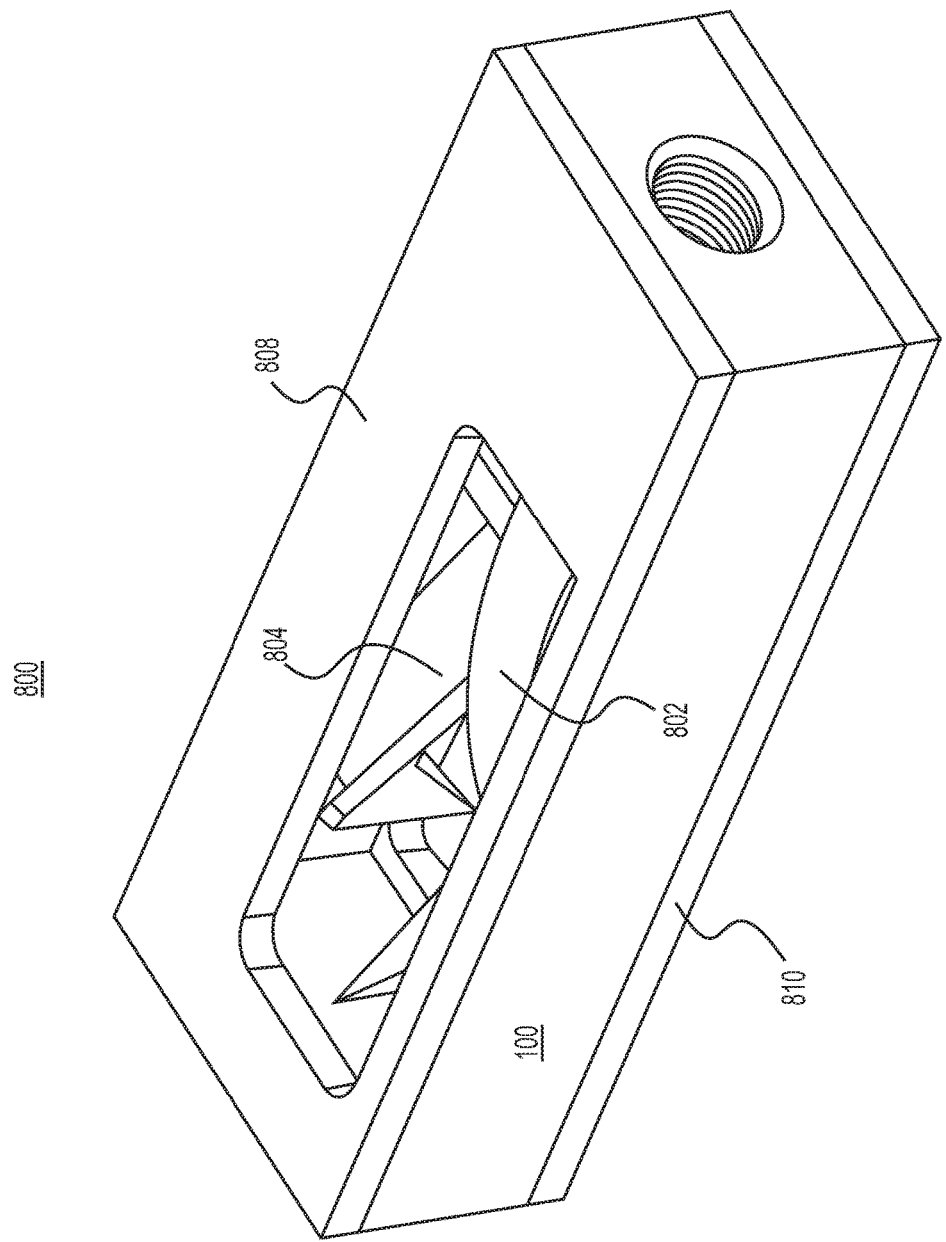

In another embodiment, as depicted in FIGS. 8A-8C, spacer 100 houses both upper anchor 802 and lower anchor 804. In other words, both the upper and lower anchors are disposed entirely within spacer 100 when the anchors are in a relaxed state. As shown in FIG. 8B, an internal drive screw 806 (i.e., an anchor drive) can be turned so that wedge 812 can be advanced forwards towards the bowed portion of both upper anchor 802 and lower anchor 804. Wedge 812 is forcibly advanced towards the bowed portion to simultaneously force upper anchor 802 and lower anchor 804 to extend through an opening arranged on superior surface 808 and inferior surface 810 of spacer 100. More precisely, as drive screw 806 is turned, wedge 812 abuts against the bowed portion of upper anchor 802 and lower anchor 804. As wedge 812 abuts against the bowed portion of the anchors, the inclined surface of wedge 810 slides along the surface of upper anchor 802 and lower anchor 804. The sliding motion applies pressure to the surfaces of the anchors, thereby forcing both upper anchor 802 and lower anchor 804 to radially extend outside of the openings of spacer 100 and into their respective intervertebral bodies.

In a further embodiment, as depicted in FIGS. 9A-9H, the anchoring device has a drive plate 906 from which upper anchor 902 and lower anchor 904 extend.

Figure 9A:
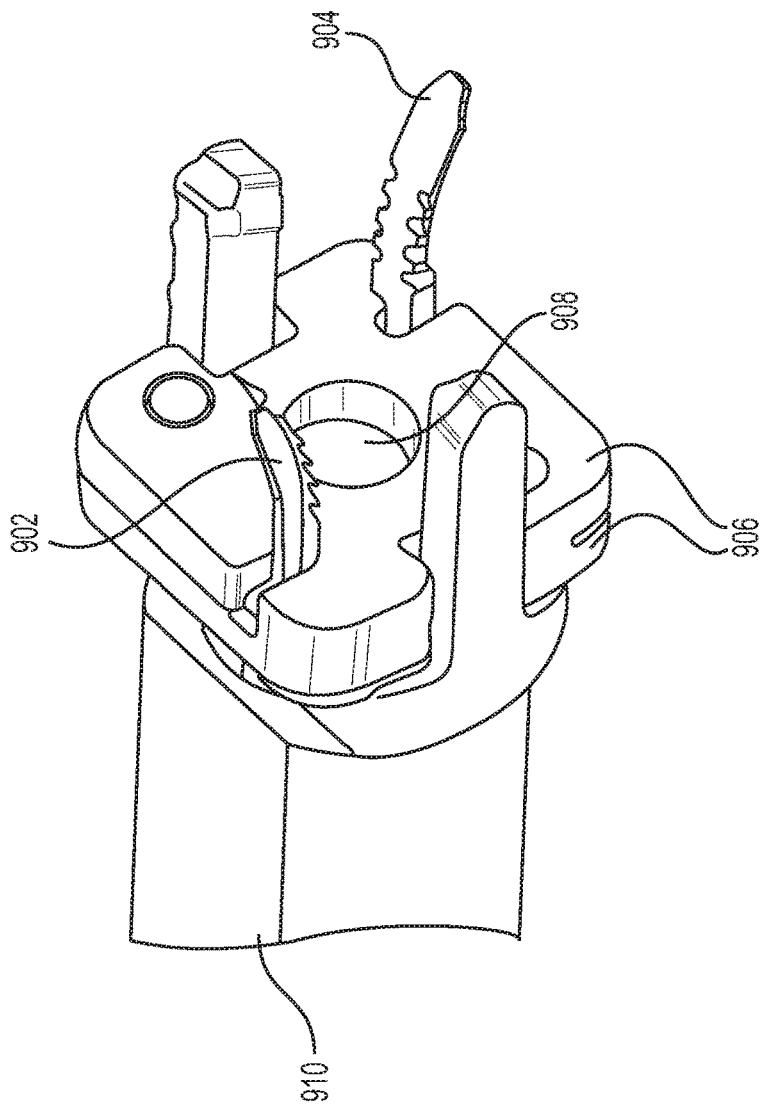
Figure 9C:
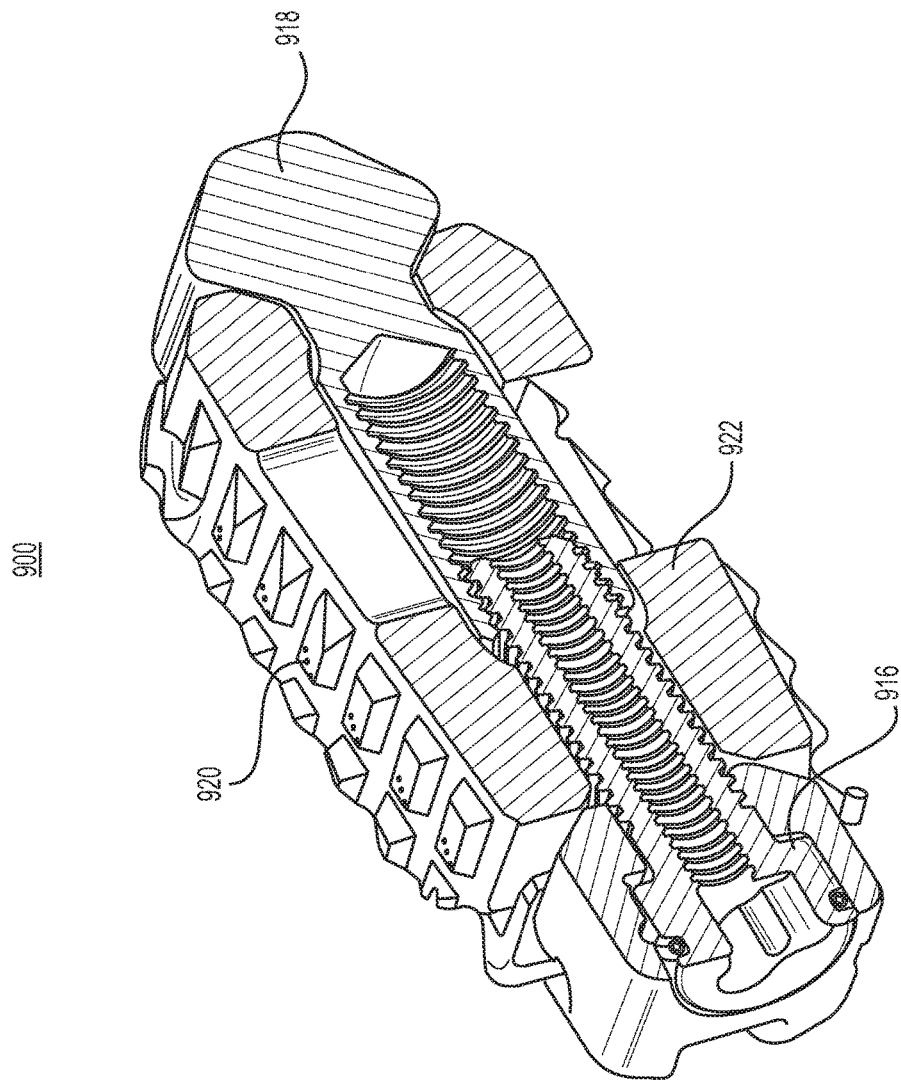

The drive plate of FIG. 9A includes through-hole 908 arranged at its central axis. The drive plate can be divided into four quadrants, with through-hole 908 being the origin point, like in a two-dimensional Cartesian plane. Upper anchor 902 extends from a first one of the quadrants (e.g., Quadrant I in a two-dimensional Cartesian plane), while lower anchor 904 extends from a second one of the quadrants (e.g., Quadrant III in the two-dimensional Cartesian plane), wherein the first and second quadrants are diagonally located from each other on drive plate 906. Although the anchors have been described as having a specific arrangement on drive plate 906, it will be clear to those skilled in the art after reading this disclosure that upper anchor 902 and lower anchor 904 can be arranged anywhere on the drive plate without departing from the scope of the present invention.

As further depicted in FIG. 9A, each of upper anchor 902 and lower anchor 906 has a pointed tip and a plurality of projections arranged on their lateral surfaces. The plurality of projections can be, for example, and without limitation, barbs that are angled away from the point in which the anchors penetrate into their respective vertebras. The barbs are advantageous because they make it difficult for the anchors to come loose, thus ensuring that the spacer is securely stabilized between the vertebras after implantation. FIG. 9A also depicts a pair of oppositely positioned grippers of holder 910 gripping onto the lateral surfaces of drive plate 906.

Figure 9D:
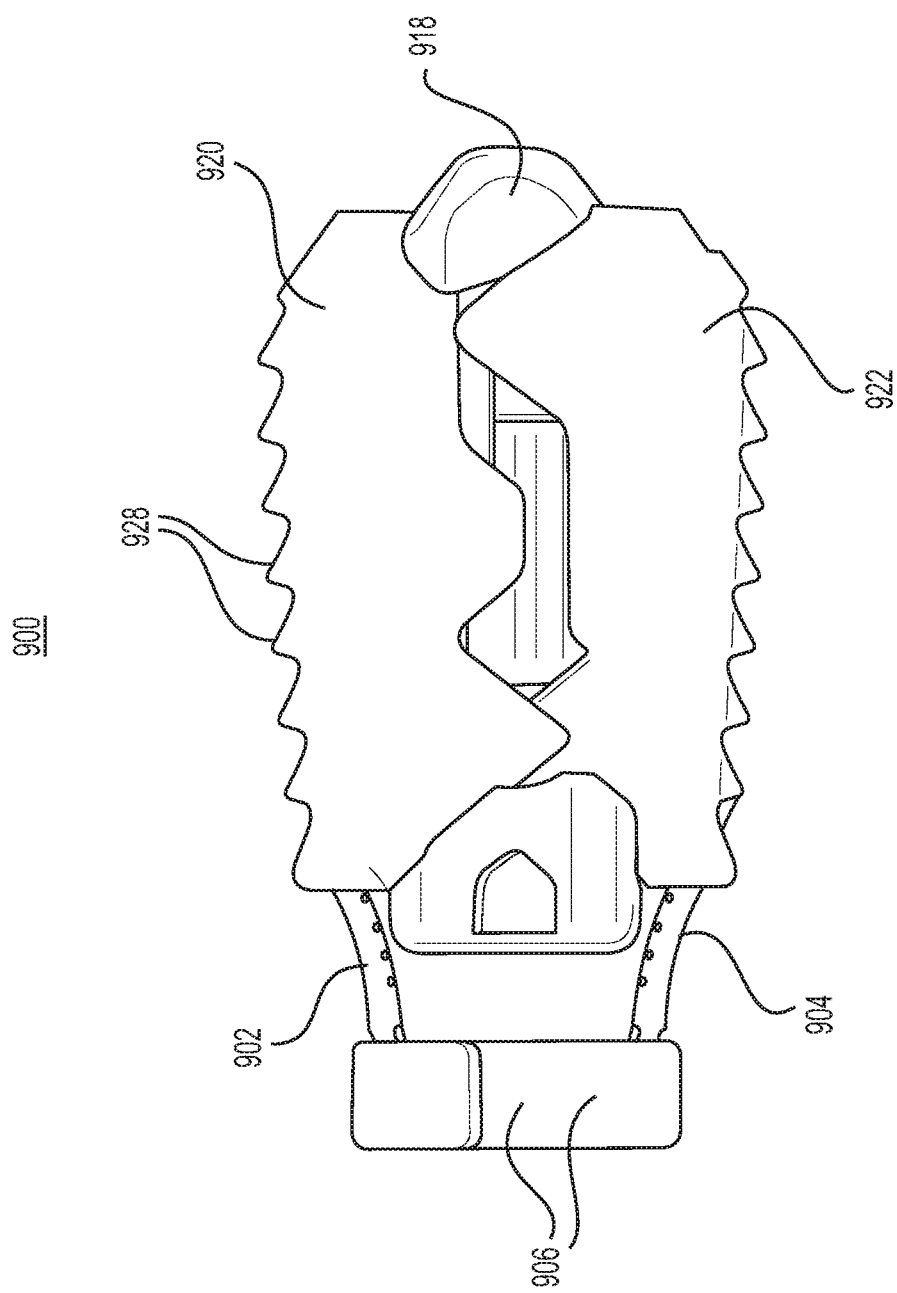

Turning now to FIG. 9B, while drive plate 906 is gripped by holder 910, a surgeon can position the grippers of holder 910 to also grip onto endplate 912 of spacer 900. Once endplate 912 is gripped by the surgeon, a driver 914 can be inserted into holder 910, which passes through through-hole 908 of drive plate 906. The driver engages one end of drive screw 916 (shown in FIG. 9C) housed within spacer 900. Once the driver has engaged the drive screw, the surgeon can turn driver 914 so that drive screw 916 can be threaded into the body of wedge 918. This causes wedge 918 to move backwards towards the proximal end of spacer 900, which in turn causes superior surface 920 and inferior surface 922 of the spacer to slide along the inclined surface of wedge 918. This can be seen more clearly in FIGS. 9C and 9D. As superior surface 920 and inferior surface 922 radially extend in opposite directions of each other, upper anchor 902 and lower anchor 904 engage upper guide 924 and lower guide 926 of spacer 900. As shown in FIG. 9D, the tips of upper anchor 902 and lower anchor 904 do not extend past the profile of teeth 928 of spacer 900, even after superior surface 920 and inferior surface 922 have been fully extended.

Figure 9E:
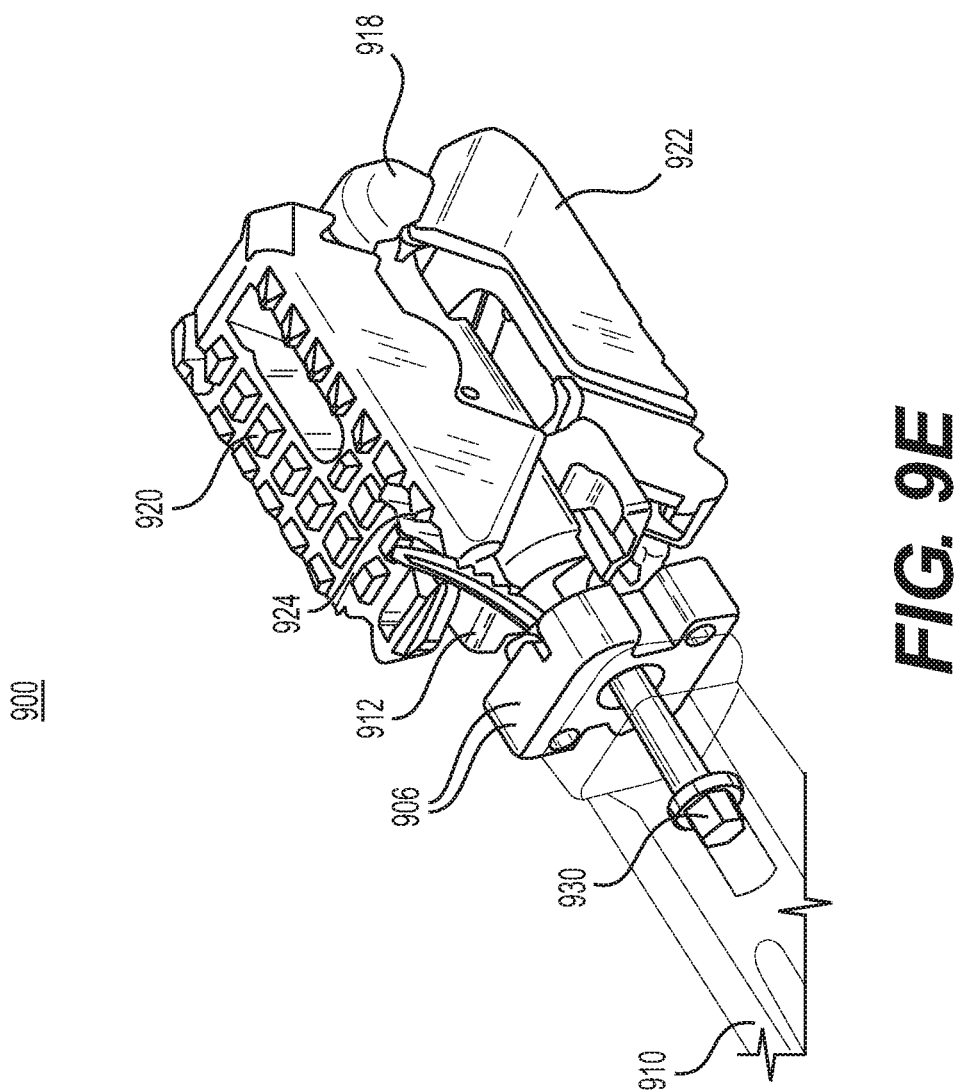
Figure 9F:
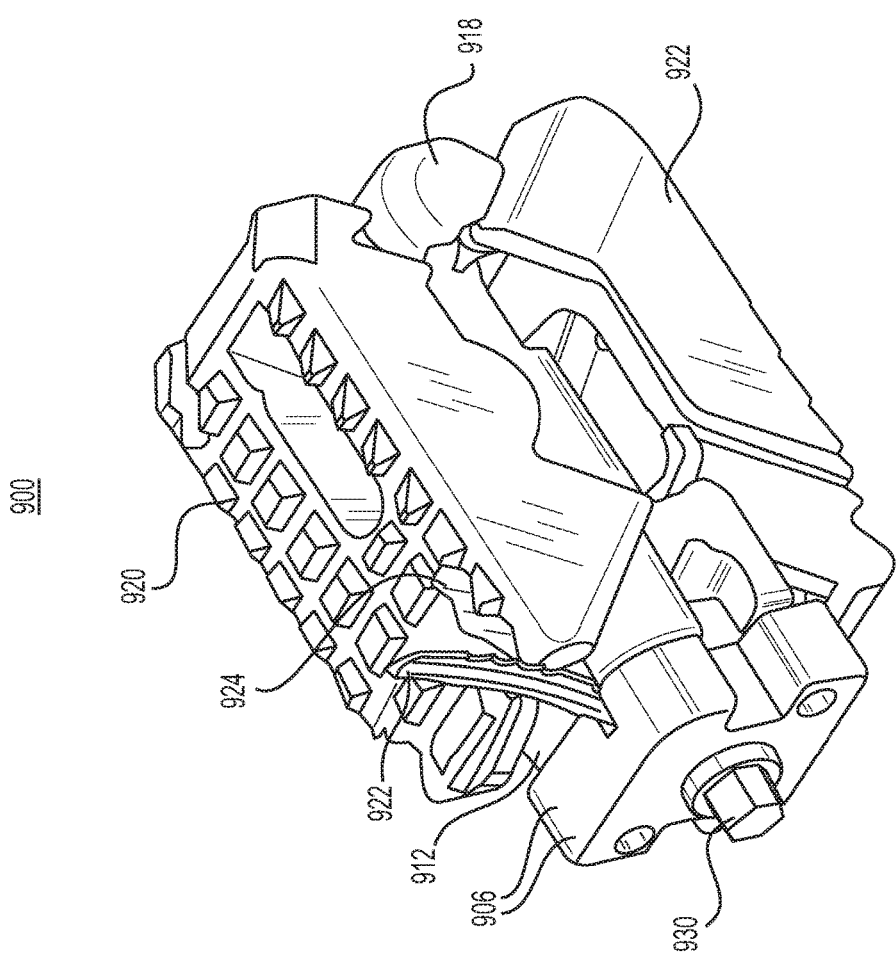
Figure 9G:
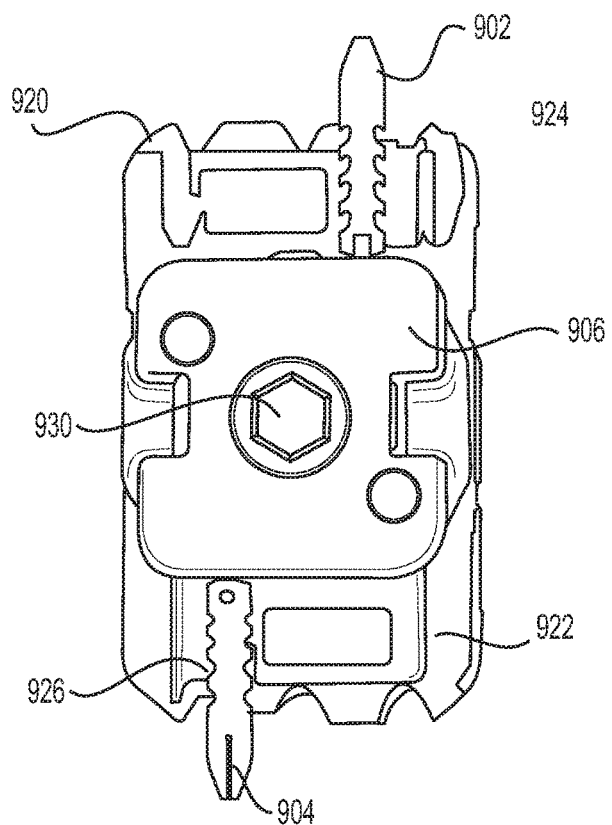
Figure 9H:
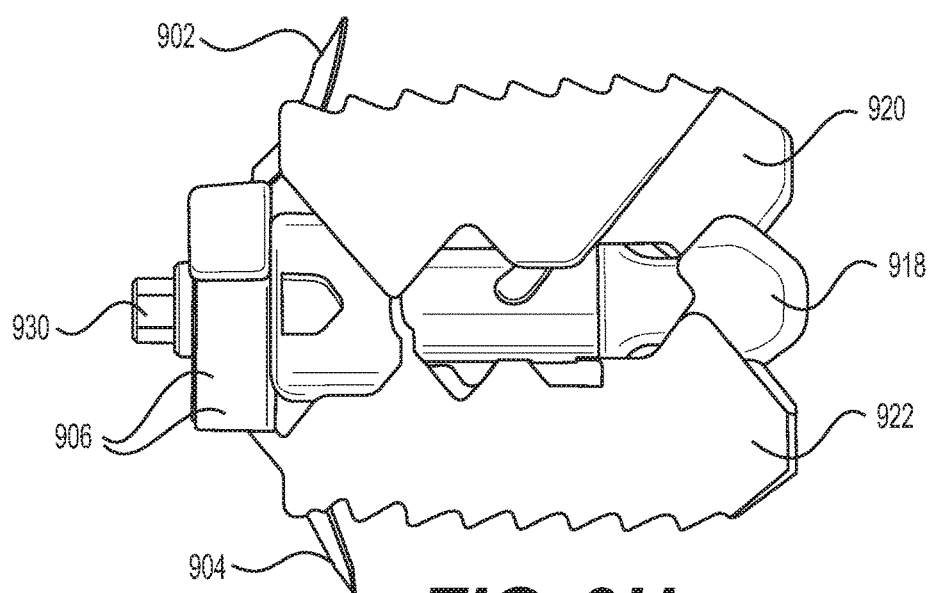

Once the superior and inferior surfaces of spacer 900 have been fully extended, the surgeon can now retract driver 914 and insert pull screw 930 (i.e., anchor driver) as shown in FIG. 9E. Pull screw 930 is physically adapted to be inserted through through-hole 908 and into the threaded hole of drive screw 916. Pull screw 930 can now be threaded to advance drive plate 906 towards the proximal end of spacer 900, which causes upper anchor 902 and lower anchor 904 to respectively slide along upper guide 924 and lower guide 926 as the drive plate is advanced towards the proximal end of the spacer. As upper anchor 902 and lower anchor 904 slide along their respective guides, the anchors simultaneously and radially extend away from spacer 900 and into their respective intervertebral bodies. Pull screw 930 is threaded by the surgeon until drive plate 906 is fully seated against endplate 912. Not only does threading pull screw 930 in this way fully deploy the anchors into their respective intervertebral bodies, it also locks the anchors to spacer 900 in a deployed position, as shown in FIGS. 9F-9H.

Figure 10:
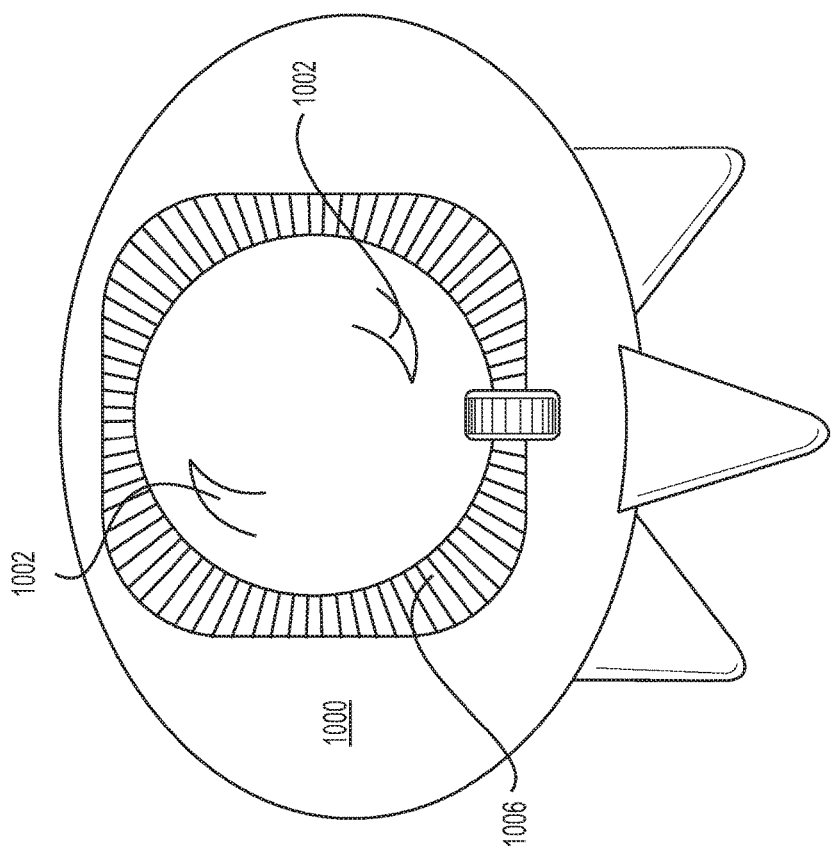
FIG. 10 depicts a spacer having worm gear for deploying one or more anchors in accordance with an alternative embodiment of the present invention.

FIG. 10 depicts a spacer-anchor combination in accordance with an alternative embodiment of the present invention. More specifically, the figure depicts spacer 1000, a plurality of upper anchors 1002, worm 1004, and gear 1006. In accordance with this embodiment, the worm is physically adapted to turn the gear, but the gear cannot turn the worm. This is because the angle on the worm is so shallow that, when the gear tries to spin it, the friction between the gear and the worm holds the worm in place. With this in mind, a surgeon can implant spacer 1000 in the disc space of adjacent vertebras. The surgeon can then use a tool to turn worm 1004 in order to rotate gear 1006 in a particular direction. As the gear rotates, upper anchors 1002 are simultaneously deployed into an intervertebral body. Once deployed, pressure from adjacent vertebras compressing down onto gear 1006 will not cause the gear to rotate. This is because, as discussed above, the angle on the worm is so shallow that the friction between the gear and the worm essentially locks the worm in place. Accordingly, upper anchors 1002 will be locked in their deployed position until worm 1004 is operated.

Figure 11:
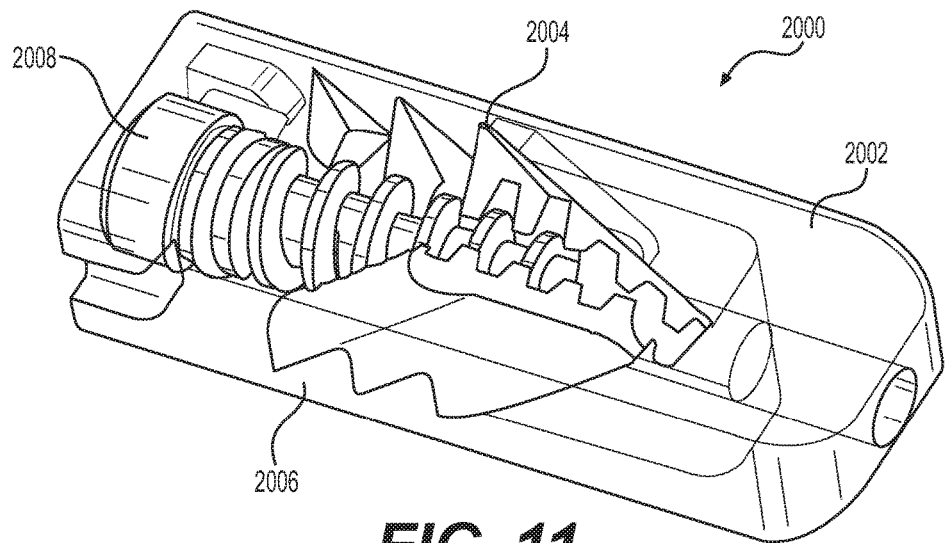
FIG. 11 depicts an implant according to another embodiment of the present invention.
Figure 12:
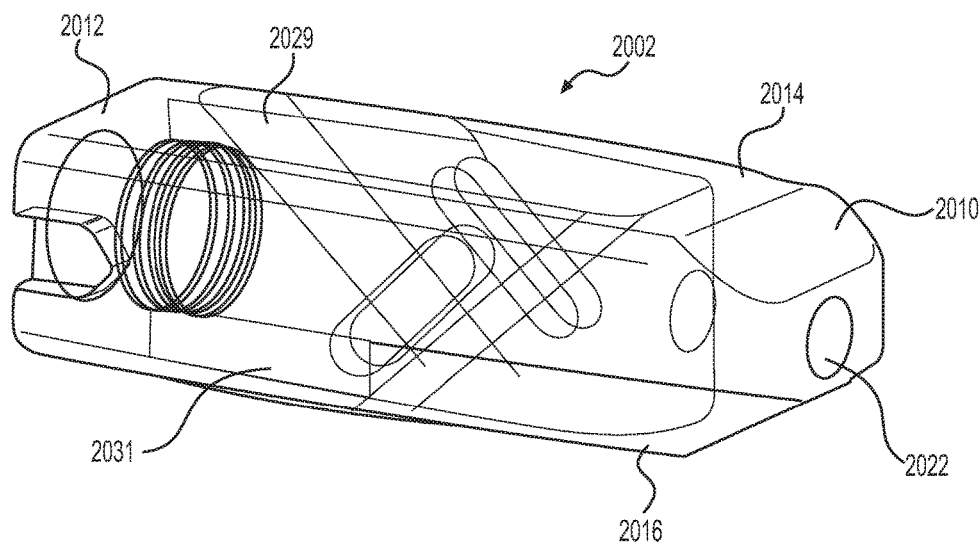
FIG. 12 depicts a spacer body of the implant illustrated in FIG. 11
Figure 13:
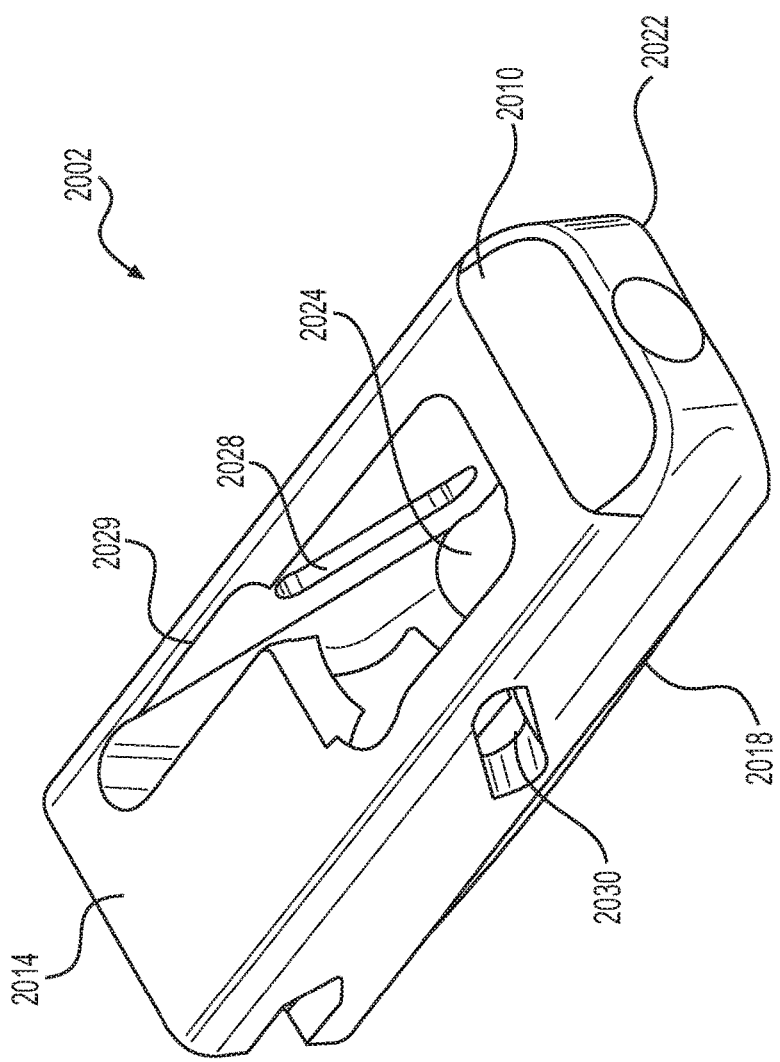
FIGS. 13 and 14 perspective views of the spacer body according to one embodiment of the present invention.
Figure 14:
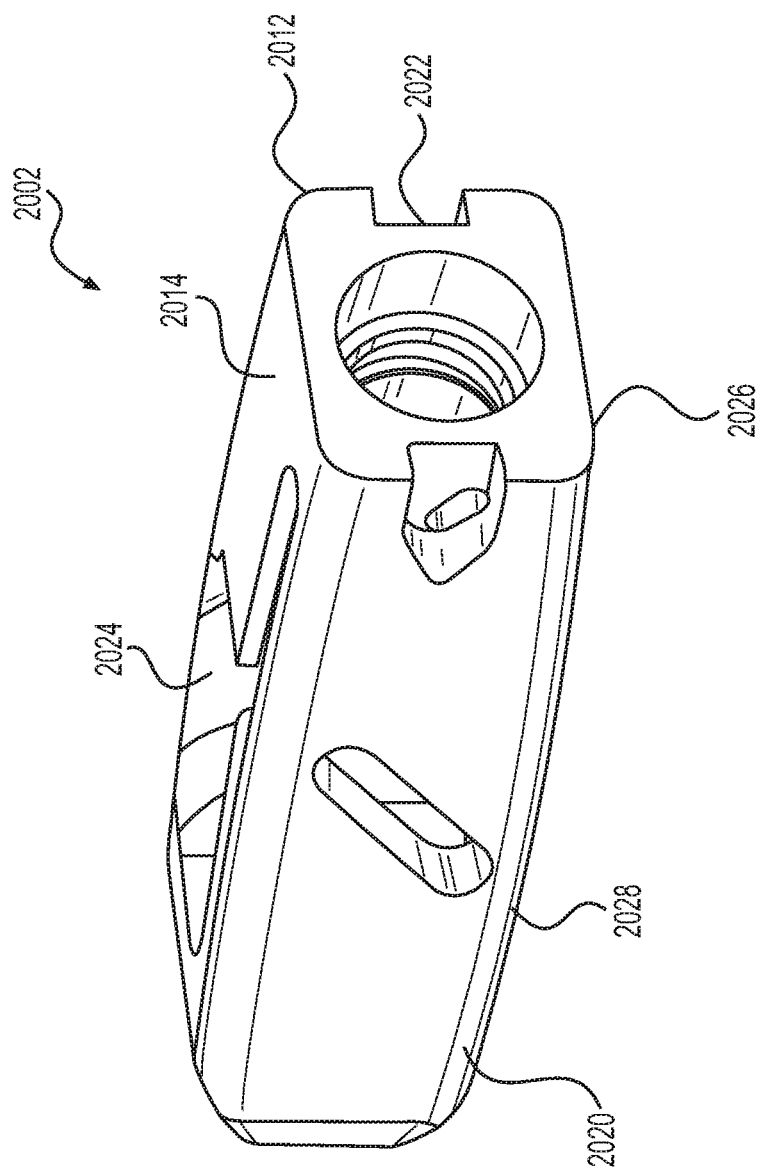

FIGS. 11-23 disclose yet another embodiment of the present invention. FIG. 11 illustrates a spinal implant 2000 that includes a spacer body 2002, a first anchor 2004, a second anchor 2006 and an actuation member 2008. The spacer body 2002 as illustrated in FIGS. 12-14 in greater detail includes an anterior portion 2010, a posterior portion 2012, a upper surface 2014, a lower surface 2016 opposing the upper surface 2014, a first lateral surface 2018 and a second lateral surface 2020. The spacer body 2002 also includes a channel 2022 that extends from the anterior portion 2010 to the posterior portion 2012. There is also a through hole 2024 that extends from the upper surface 2014 to the lower surface 2016. These features can be more clearly seen in FIGS. 13 and 14.

The upper surface 2014 and the lower surface 2016 of the spacer body 2002 may also be configured to include protrusions such teeth, ridges, and/or spikes to grip the adjacent vertebral bodies. The through-hole 2024 extending from the upper surface to the lower surface of the spacer may be configured and dimensioned to be in any geometric shape, i.e. rectangular, elliptical, or irregular. The spacer body 2002 is configured with a length, a height and a width, wherein the length of the spacer body 2002 is greater than the width. However, in other embodiments, the spacer body 2002 may be configured so that the width is greater than the length.

The anterior portion 2010 of the spacer body 2002 may be configured to be tapered for ease of insertion. The channel 2022 that extends from the anterior portion 2010 to the posterior portion 2012 has a greater diameter at a posterior portion of the spacer body 2002 than the anterior portion 2010 of the spacer body 2002. The channel 2022 extends the length of the implant so that the insertion of the implant into the intervertebral space may be accomplished anteriorly and/or posteriorly. The spacer body 2002 also includes features to retain the actuation member 2008. In the preferred embodiment, the inner surface of the posterior portion includes actuation member retention features such as notches and/or grooves which engage with a head of the actuation member 2008. It should be noted that in other embodiments the channel 2022 may be configured with ratcheting teeth that engage with the actuation member. In another alternative embodiment, the channel 2022 may include threads allowing the actuation member to translate within the implant. The translation of the actuation member then causes the anchors which are coupled to the actuation member to be guided into the adjacent vertebral bodies. Additionally, in another embodiment, the implant is provided with ramps, having similarly shaped anchors 2004, 2006. The actuation method involves pulling the anchors 2004, 2006 toward the ramp with a actuation member that is a shouldered drive screw. The shouldered drive screw is moved anteriorly or posteriorly with a nut attached to the spacer body.

Figure 20:
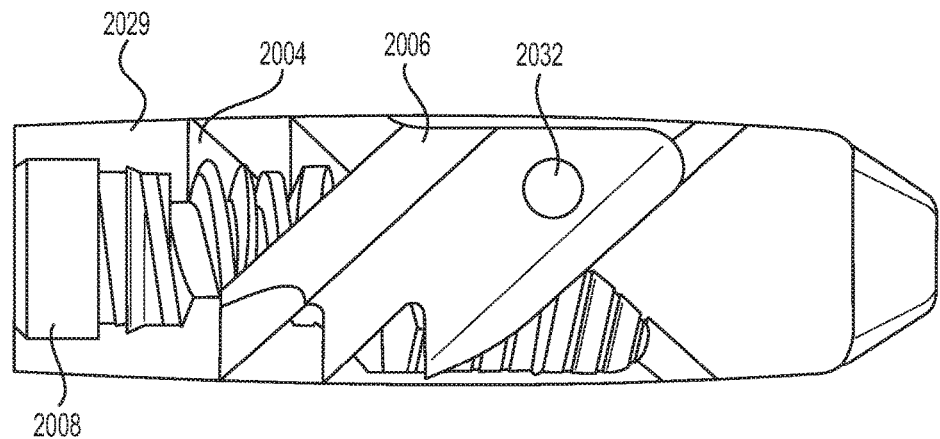
FIGS. 20 and 21 depict a lateral view of the implant when the anchors are in an undeployed and deployed state.
Figure 21:
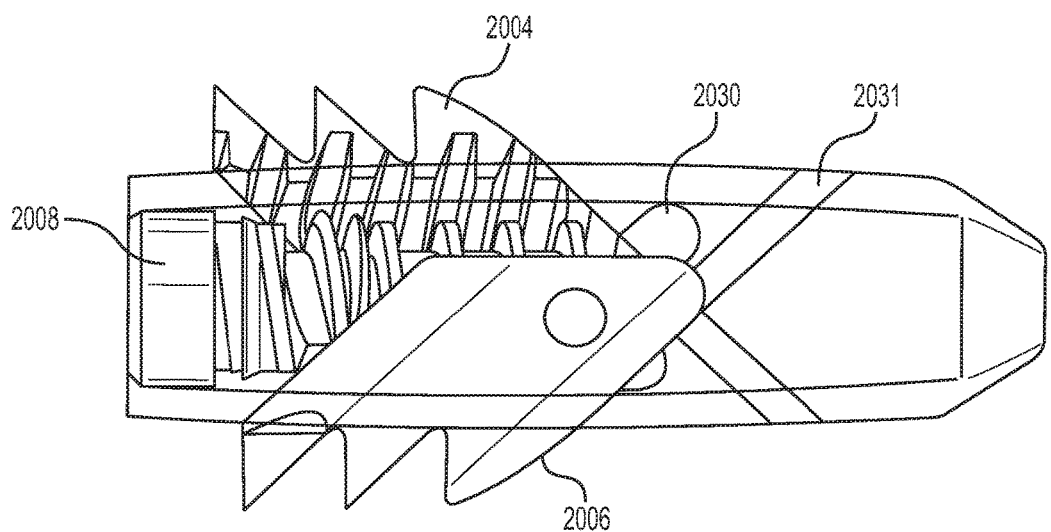

The posterior portion 2012 of the spacer body 2002 includes slots 2026 for receiving an instrument/holder as illustrated in FIG. 20. The first and second slots 2026 are configured to extend from the posterior surface of the spacer body 2002 to the first and second lateral surfaces of the spacer body 2002 respectively. The first and second lateral surfaces 2018, 2020 also include a first window 2028 and a second window 2030 which are configured to extend from the first and second lateral exterior surface to lateral inner surfaces of the spacer body 2002. The first and second windows 2028, 2030 are also configured to receive a first protrusion 2032 and a second protrusion 2032 of the anchors 2004 and 2006, which are discussed in greater detail with reference to FIGS. 15 and 16. Specifically, anchors 2004 and 2006 are positioned on the inner lateral walls of the spacer body 2002 within grooves 2029, 2031 configured on the inner surfaces of the first and second lateral walls.

Figure 18:
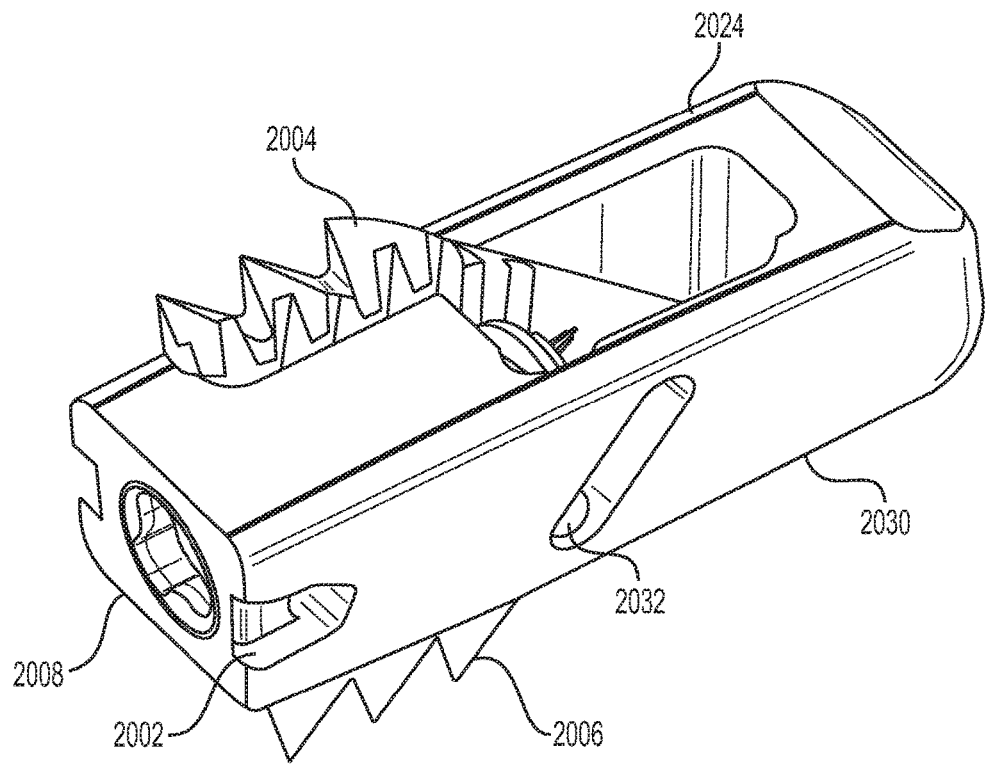
FIG. 18 depicts a perspective view of the implant of FIG. 11.

FIGS. 15 and 16 illustrate the anchors 2004, 2006 in greater detail. The anchors 2004 and 2006 have substantially the same physical and functional characteristics. Each of the anchors 2004, 2006 are with a rhomboid profile with a teeth cut. On a first side of each anchor is a protrusion 2032 that engages with the window in the spacer body 2002. On a second side of each anchor 2004, 2006 are linear cuts 2034 of a thread profile. The cuts 2034 are only interrupted by a chamfer which brings the teeth 2036 to a sharp edge. In the preferred embodiment, the anchors 2004, 2006 are configured as uncurled half-nuts. The angle between the thread profile trajectory and side profile of the anchors 2004, 2006 match the helix angle of the actuator member 2008. It should be noted that in other embodiments the anchors 2004, 2006 may be configured with different types of thread profiles that correspond to the actuator member. The anchors 2004 and 2006 once positioned within the spacer body 2002, are retained within the spacer body 2002 as the protrusions 2032 are fitted in to the windows 2030, 2032 of the lateral walls of the spacer body 2002, as shown in FIGS. 17 and 18. To enable the anchor to penetrate a vertebral body, distal portion of the anchor is tapered to form an edge. Since the anchors are made of titanium alloy, the distal portion of the anchors are sufficiently strong to pierce and penetrate through the endplate of the vertebral body. Although the anchors are preferably formed from titanium alloy, other biocompatible materials (e.g., polyetheretherketone (PEEK), other surgical grade metals, alloys, or a combination thereof) can be used to form the anchor.

The first and second anchors 2004, 2006 are separate elements that may be configured to move independently of each other along their grooves/respective guides 2029, 2031. It will also be clear from the foregoing discussion that an advantage of using the first and second anchors 2004, 2006 of the present invention is that they provide additional anchorage for stabilizing a spacer.

In operation as the anchors 2004, 2006 are moved by rotating the actuator member 2008, the protrusions 2032 positioned within the windows 2028, 2030 limit the anchors 2004, 2006 motion to a maximum distance. It should be noted that the windows 2028, 2030 may be configured to increase or decrease the amount of the maximum distance the anchors 2004, 2006 may be moved into the vertebral bodies. The angles of the windows 2028, 2030 may also be designed to provide greater or lesser angulation of the anchors 2004, 2006 when actuated into the vertebral bodies.

FIG. 18 illustrates a perspective view of the implant 2000. As shown, the spacer body 2002 includes a through hole 2024 the extends from the upper surface to the lower surface of the implant and a first groove 2029 and a second groove 2031 that extend at an angle from the lower surface to the upper surface, as illustrated in FIG. 12. The grooves 2029, 2031 are configured to receive each one of the anchors 2004, 2006. The first and second grooves 2029, 2031 act as guides so that the first groove 2029 guides the first anchor 2004 into one vertebral body and the second groove 2031 guides the second anchor 2006 into the another vertebral body. The first and second grooves 2029, 2031 are configured at an angle between the vertical and horizontal axis of the spacer body 2002. The first and second windows 2028, 2030 of the spacer are positioned within the first and second groove 2029, 2031 on the first and second lateral inner surfaces.

Figure 19:
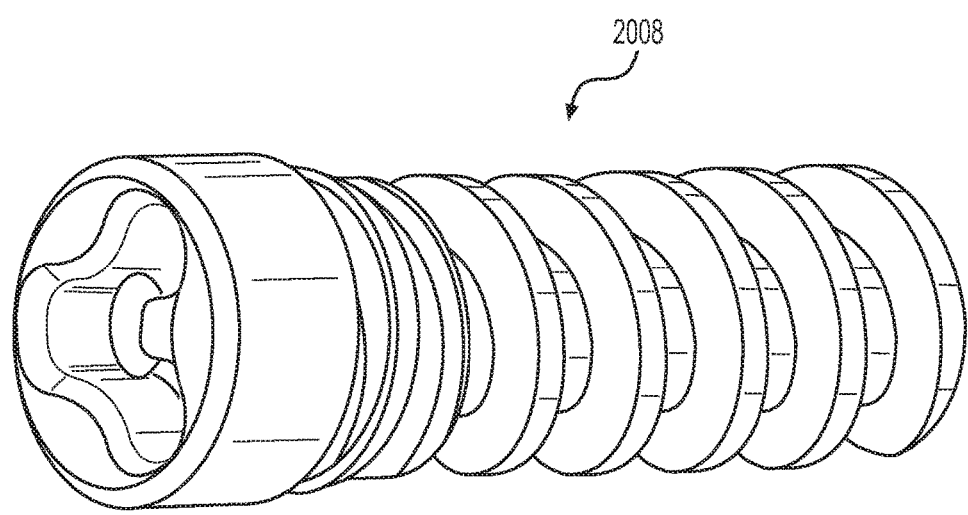
FIG. 19 depict an actuation member according to one embodiment of the present invention.

FIG. 19 shows the actuator member 2008, in the one embodiment which is a lead screw that is retained within the spacer body 2002 by pressing the screw past interfering lips in both the screw and spacer body 2002. In this embodiment the lead screw is provided with an acme thread, however most any thread profile may be used so long as the anchors 2004, 2006 have a corresponding profile. The actuation member 2008 has driving features at both ends, such as a tri-lobe and is retained within the inner walls of the posterior portion of the implant. When the actuation member 2008 is rotated, the actuation member does not translate in the longitudinal direction. However, in other embodiments, the actuation member 2008 may be configured to translate in the longitudinal direction.

Figure 22:
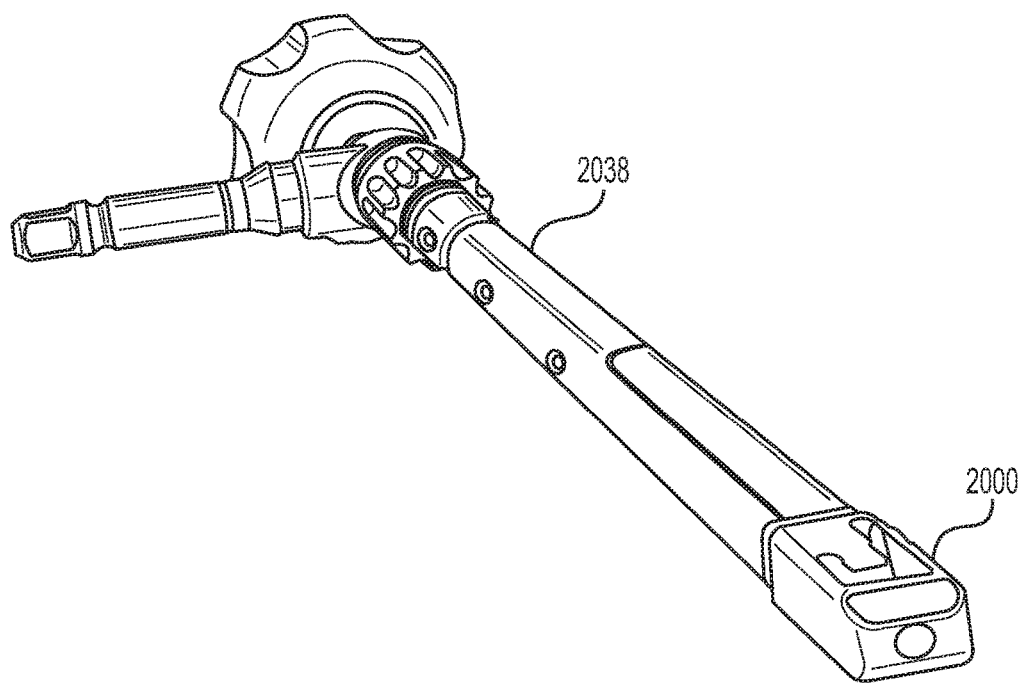
FIGS. 22 and 23 illustrate an instrument coupled to the implant when the anchors are in an undeployed and deployed state.
Figure 23:
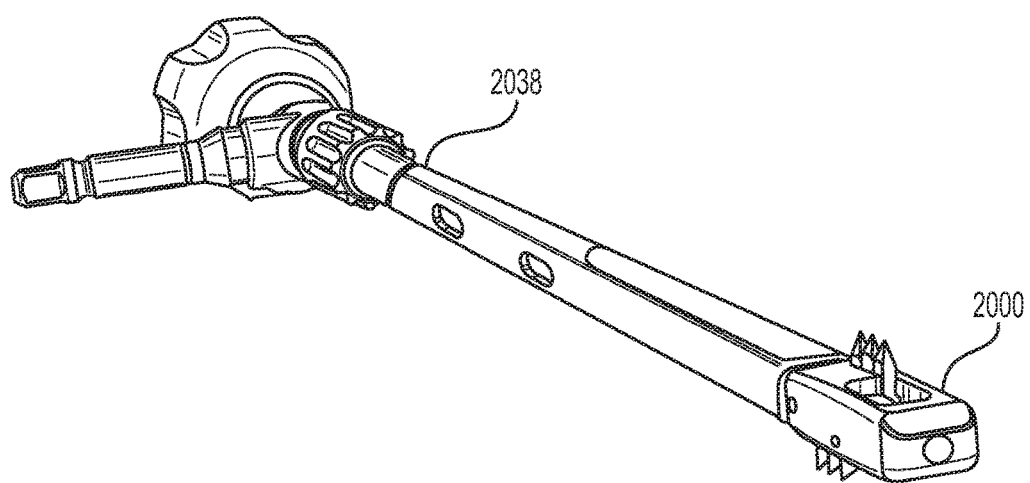

FIGS. 22 and 23 illustrates the instrument 2038 coupled to the implant in one embodiment of the invention. FIG. 22 specifically illustrates the implant and the anchors in an undeployed state and FIG. 23 illustrates the anchors 2004, 2006 in a deployed state. The instrument 2038 has a proximal end and a distal end, the distal end is configured to couple to the implant through gripping elements. The gripping elements are configured to be attached to the slots provided on the lateral surfaces of the spacer body 2002. The instrument 2038 also includes a driver element that is positioned between the gripping elements and extends from the proximal end to the distal end of the implant. The driver element is actuated by an actuation knob positioned at the proximal end of the instrument 2038. When the actuation knob is rotated in a first direction, the driver element rotates the actuation member 2008 of the implant 2000 thereby causing the anchors 2004, 2006 to move and engage with the vertebral bodies. When the actuation knob is rotated in a second direction, the driver element rotates the actuation member 2008 of the implant in a second direction, thereby causing the anchors 2004, 2006 to move to disengage with the adjacent vertebral bodies and be positioned within the spacer body 2002 of the implant. The gripping elements of the instrument 2038 are operated by the gripping knob. When the gripping knob is rotated in a first direction, the gripping elements are grip the lateral slots of the implant. When the gripping knob is rotated in a second direction, the gripping elements release the connection with the implant by loosening the grip on the lateral slots of the implant.

Now turning back to FIGS. 11, 20, and 21, the use and operation of the implant will be discussed in greater detail. The implant 2000 is positioned within the intervertebral space using the holder/instrument 2038, each one of the anchors 2004, 2006 is configured to be deployed with the rotation of the actuation member 2008 (in this case, clockwise) using the tri-lobe driver. The rotation of the actuation member 2008 draws the anchors 2004, 2006 proximally which also drives them up the grooves 2029, 2031 of the spacer body. This can be reversed by turning the actuation member 2008 the other way. Specifically, the anchors 2004, 2006 are moved or translated into the corresponding vertebral bodies when the actuation member 2008 is rotated in a first direction. When the actuation member 2008 is rotated in a second direction, the anchors 2004, 2006 are moved to be positioned back within the spacer body 2002. In one embodiment, as the actuation member 2008 is rotated, one anchor 2004 is guided towards the upper vertebral body and the second anchor 2006 is guided towards the lower vertebral body. The first and second anchors 2004, 2006 are guided simultaneously when the actuation member 2008 is actuated. However, in other embodiments, the first and second anchors 2004, 2006 may be moved independently of each other with one actuation member 2008. In another embodiment, there may be provided with at least two actuation members that engage with each one of the anchors, thereby enabling each one of the anchors to be independently moved with respect to the other anchor.

As illustrated in FIG. 11, each of the anchors 2004, 2006 are configured to mate and correspond with the threads of the actuation member. As the actuation member is rotated, the threads of the actuation member 2008 engage the partial threads of the anchors 2004, 2006, applying force on the anchors 2004, 2006. The force applied by the actuation member 2008 causes the anchors 2004, 2006 to move within the respective grooves 2029, 2031 of the inner walls of the spacer body 2002. The grooves 2029, 2031 guide each of the anchors 2004, 2006 as force is applied on the anchors, towards the upper and lower vertebral bodies.

The anchors 2004, 2006 are limited in movement by the protrusions 2032 positioned within the windows 2030 of the lateral walls. In some embodiments, the windows 2030 can be configured with a radius and/or different angles thereby provided varying movement of the anchors in to the vertebral bodies. Additionally, the actuation member 2008 may be driven from the other end using the smaller driving feature through the hole in the anterior surface of the of the spacer body 2002. In other contemplated embodiments, the actuation member 2008 rather than being rotated can be translated in a longitudinal axis from a posterior portion of the implant to the anterior portion of the implant causing the anchors 2004, 2006 to be deployed into the adjacent vertebral bodies. In another embodiment, the actuation member 2008 can be ratcheting instrument which ratchets the anchors into the adjacent vertebral bodies.

It is to be understood that the disclosure describes a few embodiments and that many variations of the invention can easily be devised by those skilled in the art after reading this disclosure and that the scope of the present invention is to be determined by the following claims.

What is claimed is:
1. An intervertebral fusion device comprising:
   a spacer adapted to be implanted between an upper vertebral body and a lower vertebral body;
   a first anchor and a second anchor positioned within the spacer; and an actuation screw positioned within the spacer and adapted to engage with the first anchor and the second anchor, wherein when the actuation screw is actuated in a first direction, the first anchor moves to engage the upper vertebral body and the second anchor moves to engage the lower vertebral body, wherein the first anchor and the second anchor are configured to be moved simultaneously, and wherein each of the first and second anchors includes a first side and a second side opposite the first side, the second side including a plurality of linear cuts configured to engage with the actuation screw.

2. The intervertebral fusion device of claim 1, wherein the first and second anchors in an undeployed state are disposed entirely within the spacer.

3. The intervertebral fusion device of claim 1, wherein the spacer has an upper guide and a lower guide that are adapted to respectively guide deployment of the first and second anchors into their respective vertebral bodies.

4. The intervertebral fusion device of claim 3, wherein the first and second anchors are separate elements that move independently of each other along their respective upper and lower guides when force is applied to the first and second anchors.

5. The intervertebral fusion device of claim 3, wherein each of the upper and lower guides has an inclined surface that presses against a respective one of the first and second anchors to deploy them into their respective vertebral bodies.

6. The intervertebral fusion device of claim 5, wherein the first and second anchors respectively have an inclined edge that is substantially the same as the inclined surface of the upper and lower guides.

7. The intervertebral fusion device of claim 3, wherein the spacer includes a first window and second window positioned within the upper and lower guides.

8. The intervertebral fusion device of claim 7, wherein the first anchor and the second anchor include a first and second protrusions, respectively, the first and second protrusions being positioned within the first and second windows.

9. The intervertebral fusion device of claim 1, wherein the plurality of linear cuts form partial threads that interconnect with threads of the actuation screw.

10. The intervertebral fusion device of claim 1, wherein the spacer includes a pair of oppositely positioned lateral slots for receiving a gripper of an implantation instrument.

11. An intervertebral fusion device comprising:
a spacer adapted to be implanted between an upper vertebral body and a lower vertebral body;
a first anchor and a second anchor positioned within the spacer; and
an actuation screw positioned within the spacer and adapted to engage with the first anchor and the second anchor, wherein when the actuation screw is actuated in a first direction, the first anchor moves to engage the upper vertebral body and the second anchor moves to engage the lower vertebral body, wherein the first anchor and the second anchor are configured with a rhomboid profile, and wherein each of the first and second anchors includes a first side and a second side opposite the first side, the second side including a plurality of linear cuts configured to engage with the actuation screw.

12. The intervertebral fusion device of claim 11, wherein the first and second anchors in an undeployed state are disposed entirely within the spacer.

13. The intervertebral fusion device of claim 1, wherein the spacer has an upper guide and a lower guide that are adapted to respectively guide deployment of the first and second anchors into their respective vertebral bodies.

14. The intervertebral fusion device of claim 13, wherein the first and second anchors are separate elements that move independently of each other along their respective upper and lower guides when force is applied to the first and second anchors.

15. The intervertebral fusion device of claim 13, wherein each of the upper and lower guides has an inclined surface that presses against a respective one of the first and second anchors to deploy them into their respective vertebral bodies.

16. The intervertebral fusion device of claim 15, wherein the first and second anchors respectively have an inclined edge that is substantially the same as the inclined surface of the upper and lower guides.

17. The intervertebral fusion device of claim 11, wherein the plurality of linear cuts form partial threads that interconnect with threads of the actuation screw.

18. An intervertebral fusion device comprising:
a spacer adapted to be implanted between an upper vertebral body and a lower vertebral body;
a first anchor and a second anchor positioned within the spacer; and
a screw positioned within the spacer and adapted to engage with the first anchor and the second anchor, wherein when the actuation screw is actuated in a first direction, the first anchor moves to engage the upper vertebral body and the second anchor move to engage the lower vertebral body, wherein threads of the screw are interconnected with threads of the first and second anchors, and wherein each of the first and second anchors includes a first side and a second side opposite the first side, the second side including a plurality of linear cuts configured to engage with the actuation screw.

* * * * *